US012174194B2

(12) United States Patent
Kumaki et al.

(10) Patent No.: US 12,174,194 B2
(45) Date of Patent: Dec. 24, 2024

(54) TUMOR MARKER, AND METHOD FOR COLLECTING AND DETECTING TUMOR CELL IN DISTINCTION FROM CONTAMINANT CELL

(71) Applicant: TOSOH CORPORATION, Yamaguchi (JP)

(72) Inventors: Yuichi Kumaki, Kanagawa (JP); Sayaka Hirai, Kanagawa (JP); Makoto Otsuki, Kanagawa (JP); Daisuke Miki, Kanagawa (JP); Toru Futami, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 1054 days.

(21) Appl. No.: 16/978,887

(22) PCT Filed: Feb. 27, 2019

(86) PCT No.: PCT/JP2019/007470

§ 371 (c)(1),
(2) Date: Sep. 8, 2020

(87) PCT Pub. No.: WO2019/172030

PCT Pub. Date: Sep. 12, 2019

(65) Prior Publication Data

US 2020/0408769 A1 Dec. 31, 2020

(30) Foreign Application Priority Data

Mar. 9, 2018 (JP) ................................ 2018-042710
Jun. 1, 2018 (JP) ................................ 2018-105966
Oct. 12, 2018 (JP) ................................ 2018-193273

(51) Int. Cl.

*G01N 33/574* (2006.01)
*C07K 14/47* (2006.01)
*C07K 14/705* (2006.01)
*C07K 14/745* (2006.01)
*C12Q 1/6886* (2018.01)

(52) U.S. Cl.

CPC ... *G01N 33/57492* (2013.01); *C07K 14/4725* (2013.01); *C07K 14/705* (2013.01); *C07K 14/70578* (2013.01); *C07K 14/745* (2013.01); *C12Q 1/6886* (2013.01); *C12Q 2600/158* (2013.01)

(58) Field of Classification Search

CPC .......... G01N 33/57492; C07K 14/4725; C07K 14/705; C07K 14/70578; C07K 14/745; C12Q 1/6886; C12Q 2600/158

See application file for complete search history.

(56) References Cited

U.S. PATENT DOCUMENTS

2004/0063120 A1* 4/2004 Beer ................ G01N 33/57423 435/6.14
2006/0134122 A1* 6/2006 Rapraeger .......... C07K 16/2896 536/23.53
2006/0177453 A1* 8/2006 Mather ............. A61K 47/6849 536/23.53
2008/0020979 A1* 1/2008 Rapraeger .............. A61P 43/00 514/4.8
2009/0298170 A1* 12/2009 D'Amour ............. C12N 5/067 435/377
2011/0003008 A1* 1/2011 Lim ......................... A61P 9/00 435/317.1
2012/0004117 A1* 1/2012 Aburatani ........ G01N 33/57492 506/7
2013/0040849 A1* 2/2013 Eliasson .......... G01N 33/57434 530/389.1
2013/0209493 A1 8/2013 Garcia-Blanco et al.
2014/0011746 A1* 1/2014 Rapraeger ............ A61K 38/177 514/21.3
2014/0093496 A1* 4/2014 Mimoto ................. A61P 11/02 435/69.6
2014/0141986 A1* 5/2014 Spetzler ............... C12Q 1/6886 435/7.1

(Continued)

FOREIGN PATENT DOCUMENTS

EP 2309273 A1 4/2011
JP 2008-533487 A 8/2008

(Continued)

OTHER PUBLICATIONS

Kim (Cell Oncol. 2014 Vol. 37, p. 235-243 (Year: 2014).*
International Search Report for PCT Patent App. No. PCT/JP2019/007470 (May 28, 2019).
Partial Supplementary European Search Report for European Patent App. No. 19764529.4 (Oct. 22, 2021).
Kim, M.-J., et al., "Identification of novel markers that outperform EpCAM in quantifying circulating tumor cells," Cell. Oncol. 2014;37:235-243.

(Continued)

*Primary Examiner* — Changhwa J Cheu
(74) *Attorney, Agent, or Firm* — Cermak & McGowan LLP; Shelly Guest Cermak

(57) ABSTRACT

A method of collecting and detecting a tumor cell contained in a sample in distinction from a contaminant cell is provided. The tumor cell contained in the sample are collected and detected in distinction from the contaminant cell by detecting any of the following polypeptides or a gene encoding the polypeptide present in the sample: (i) a polypeptide containing at least the amino acid sequence of any of six sequences such as TM4SF1 (GenBank No. NP_055035.1) and TNFRSF12A (GenBank No. NP_057723.1); (ii) a polypeptide containing at least an amino acid sequence having a homology of not less than 70% to the amino acid sequence described above; and (iii) a polypeptide containing at least a splicing variant of the amino acid sequence (the amino acid sequence of (i) or (ii) described above).

6 Claims, 13 Drawing Sheets

Specification includes a Sequence Listing.

(56) References Cited

U.S. PATENT DOCUMENTS

| | | | | |
|---|---|---|---|---|
| 2014/0148350 | A1 | 5/2014 | Spetzler et al. | |
| 2014/0162888 | A1 | 6/2014 | Kuslich et al. | |
| 2014/0329243 | A1 | 11/2014 | Barthelemy et al. | |
| 2015/0301055 | A1 | 10/2015 | Spetzler | |
| 2015/0323538 | A1* | 11/2015 | Whitsett | C12Q 1/6886 435/7.1 |
| 2016/0041153 | A1 | 2/2016 | Brown et al. | |
| 2018/0282692 | A1* | 10/2018 | Rawlings | C12N 9/22 |

FOREIGN PATENT DOCUMENTS

| | | | | |
|---|---|---|---|---|
| JP | 2013-526852 | A | 6/2013 | |
| JP | 2013-540995 | A | 11/2013 | |
| JP | 2014-507160 | A | 3/2014 | |
| JP | 2014-533828 | A | 12/2014 | |
| JP | 2017-083247 | A | 5/2017 | |
| WO | WO2006/018290 | A2 | 2/2006 | |
| WO | WO2006/104474 | A2 | 10/2006 | |
| WO | WO-2009064789 | A2 * | 5/2009 | C07K 16/2887 |
| WO | WO-2014198817 | A1 * | 12/2014 | A61K 31/282 |
| WO | WO-2015054427 | A1 * | 4/2015 | A61K 47/6849 |

OTHER PUBLICATIONS

Kim, M.-J., et al., "Supplementary Materials Identification of Novel Markers that Outperform EpCAM in Quantifying Circulating Tumor Cells," Cell. Oncol. 2014;37:235-243.

Shahneh, F. Z., "Sensitive antibody-based CTCs detection from peripheral blood," Human Antibodies 2013;22:51-54.

Cao, J., et al., "TM4SF1 Promotes Gemcitabine Resistance of Pancreatic Cancer In Vitro and In Vivo," PLOS ONE 2015;10:e0144969, 13 pp.

Office Action and Search Report dated Jan. 18, 2023 issued in corresponding Chinese Patent App. No. 201980018046.7 with machine translation.

Transmembrane 4 L6 family member 1 [*Homo sapiens*], Protein, NCBI, NCBI Reference Sequence: NP_055035.1, 5 pp., Mar. 4, 2018, retrieved from the internet on Jan. 12, 2023.

Office Action dated Aug. 31, 2023 issued in corresponding EP Patent App. No. 19764529.4.

Supplementary Materials, Min Ji et al, Cell Oncology, (2014); 37(4), 235-243 [XP093076389] Table S4.

* cited by examiner

[Fig. 1]
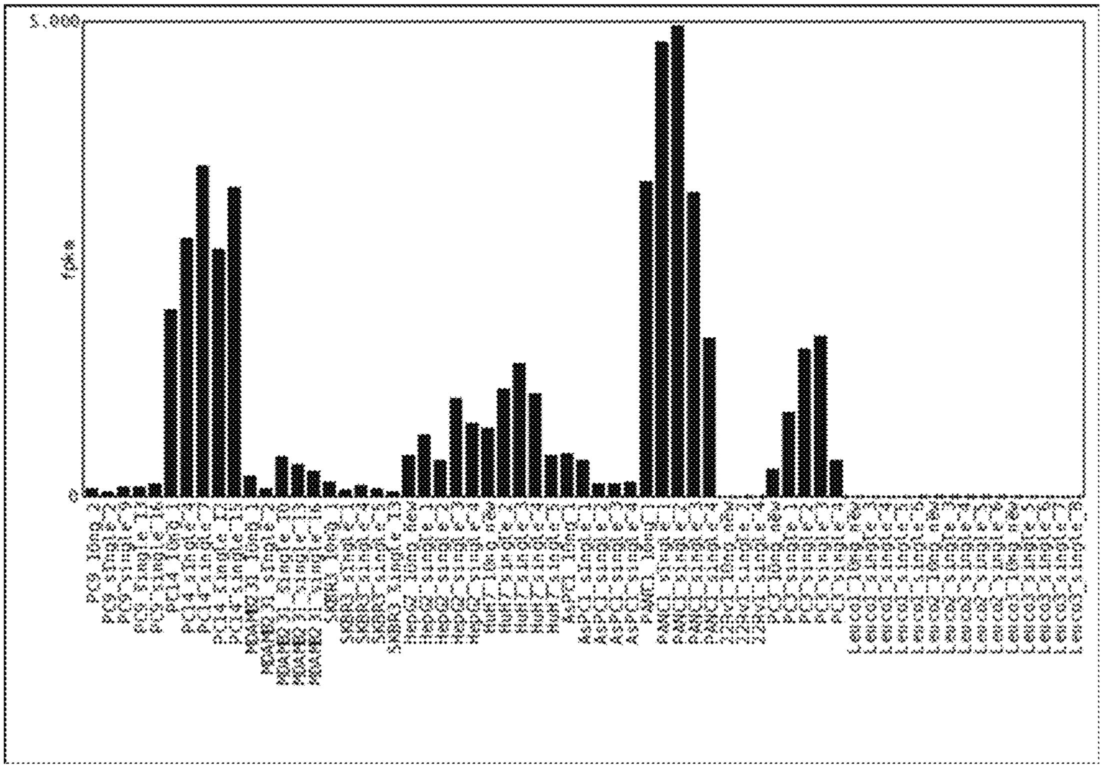

[Fig. 2]
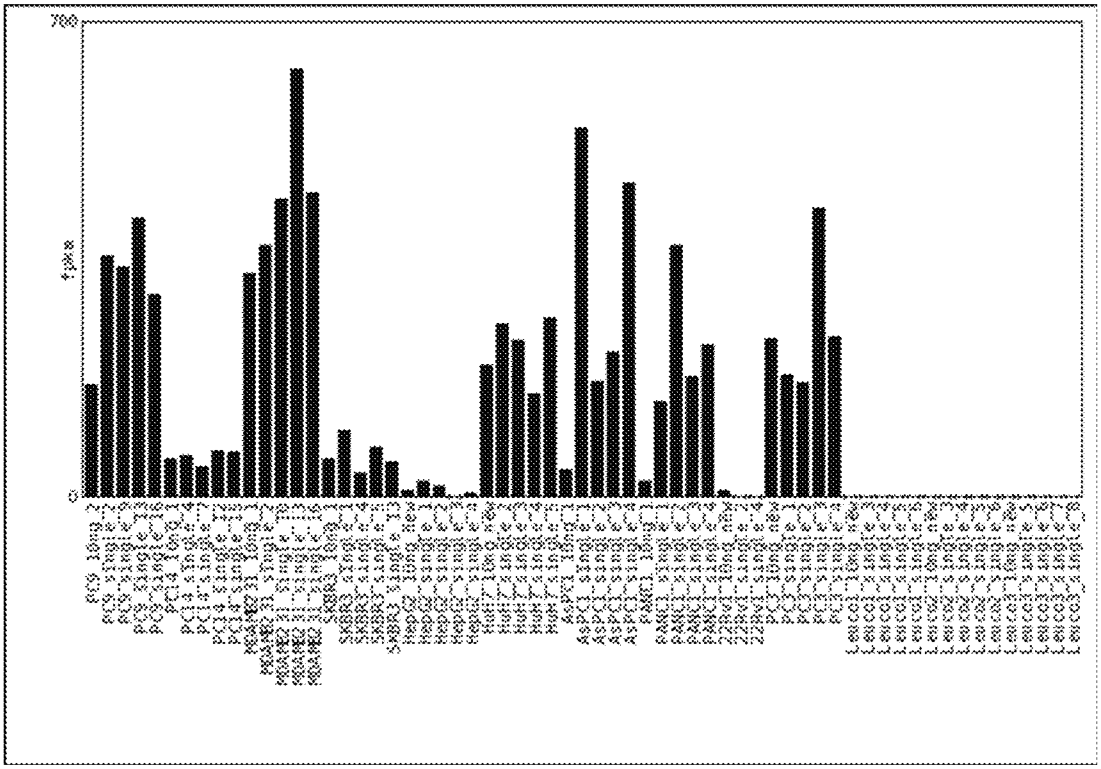

[Fig. 3]
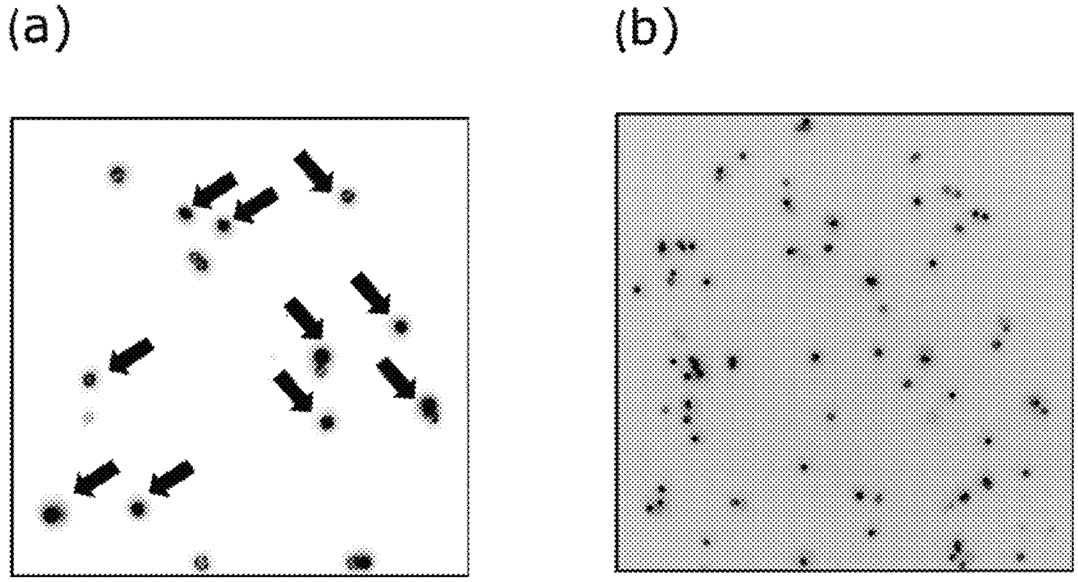

[Fig. 4]
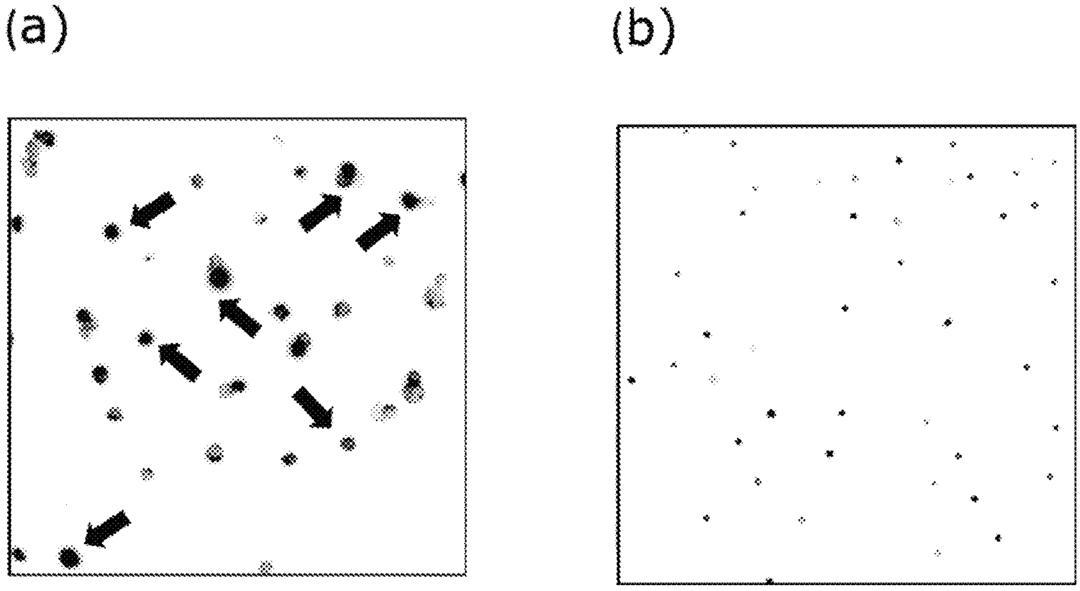

[Fig. 5]
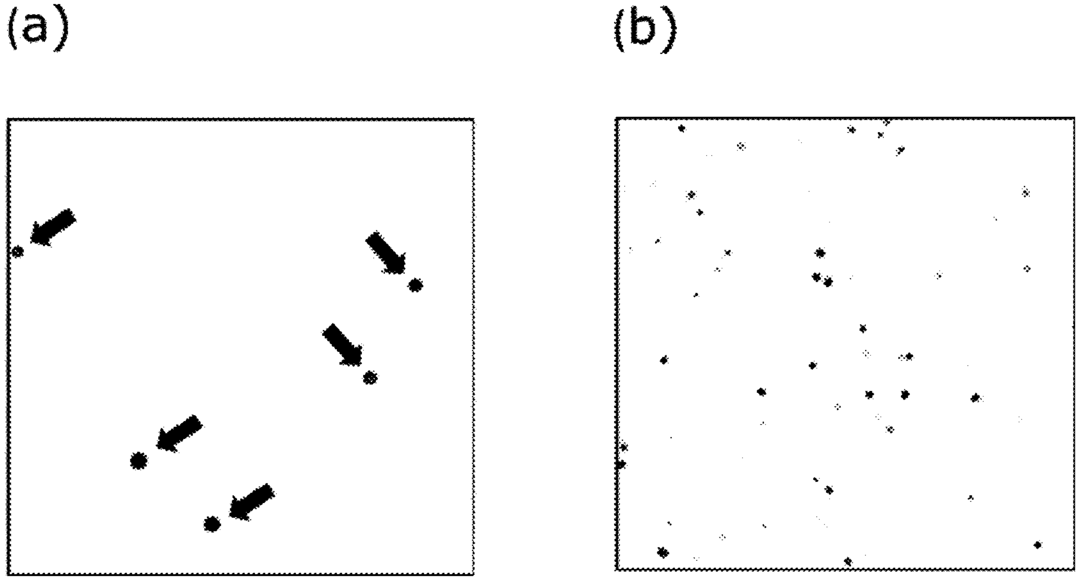

[Fig. 6]
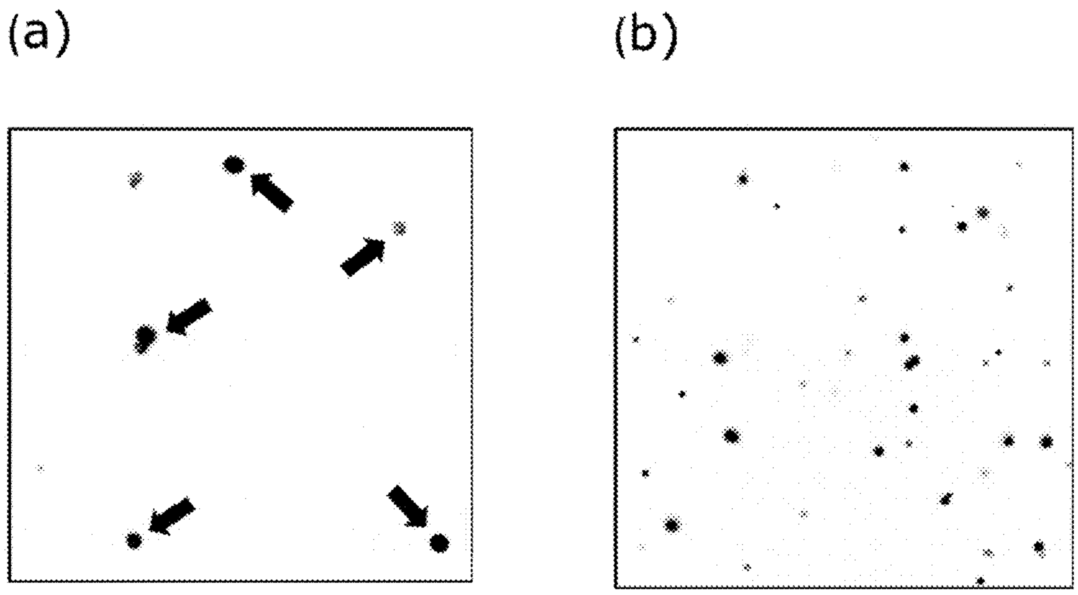

[Fig. 7]
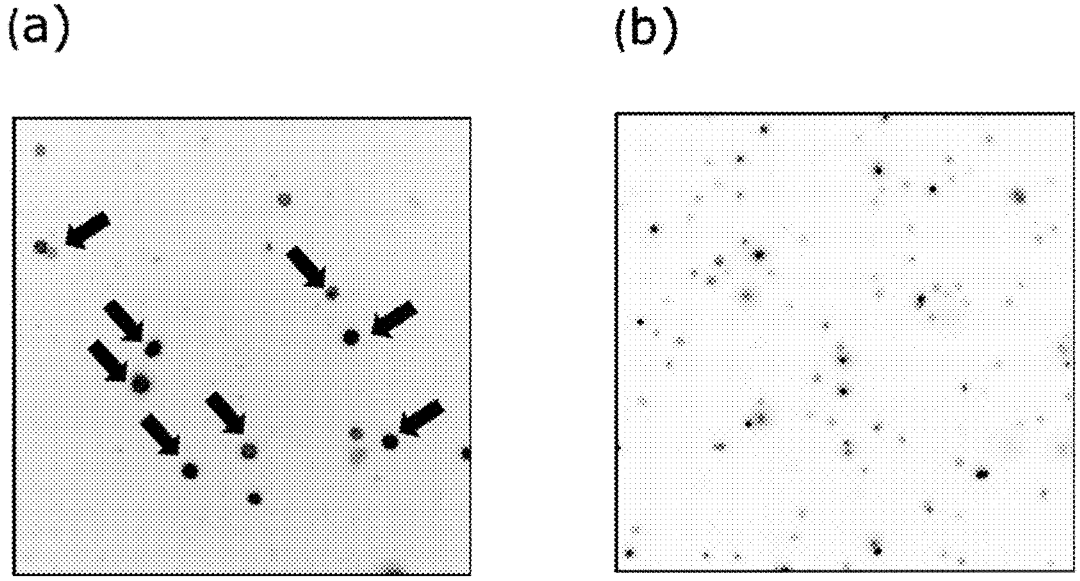

[Fig. 8]
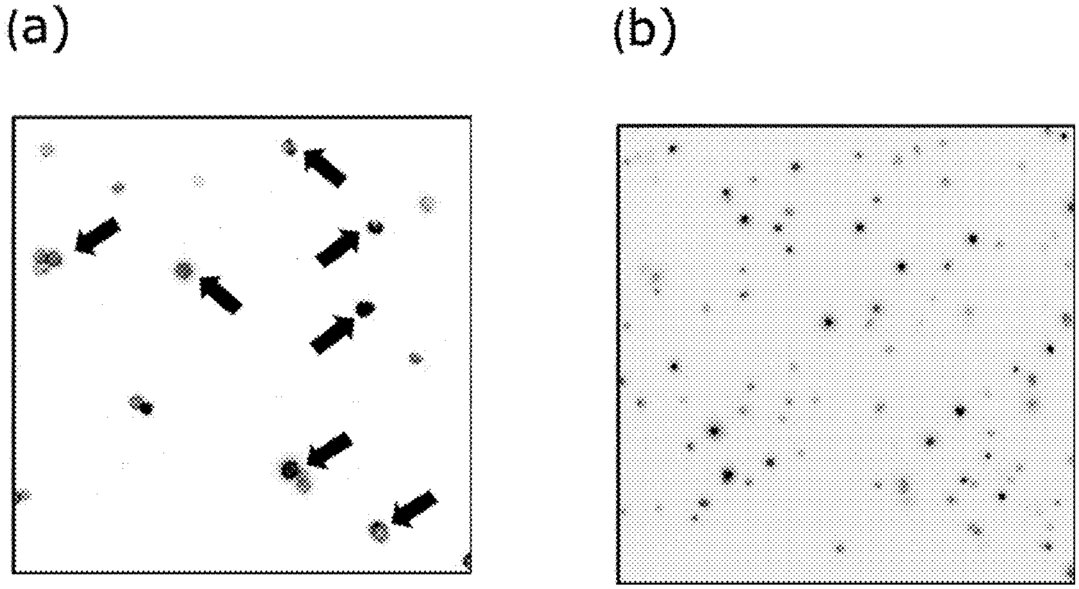

[Fig. 9]
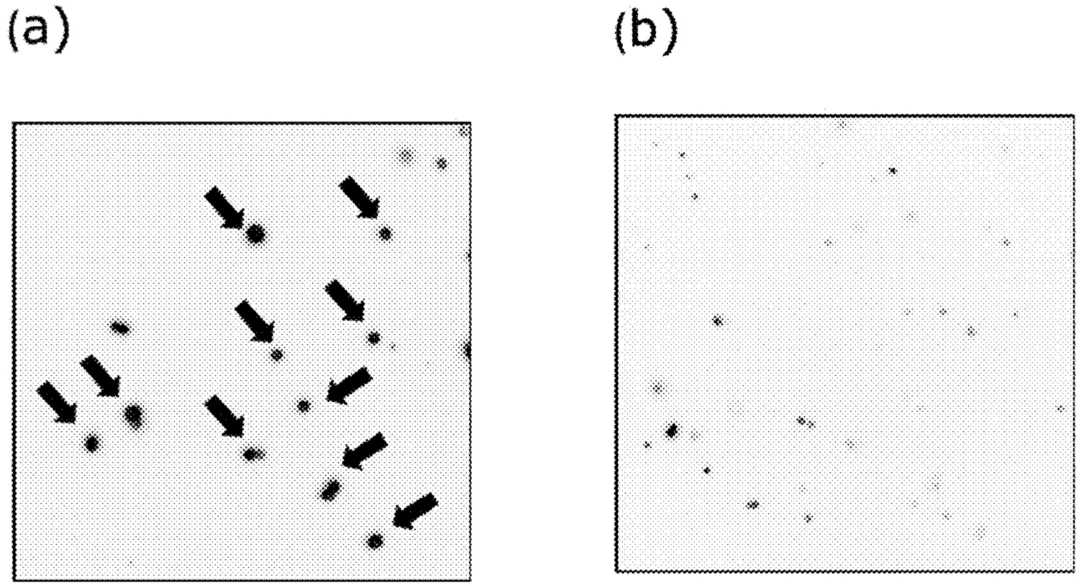

[Fig. 10]
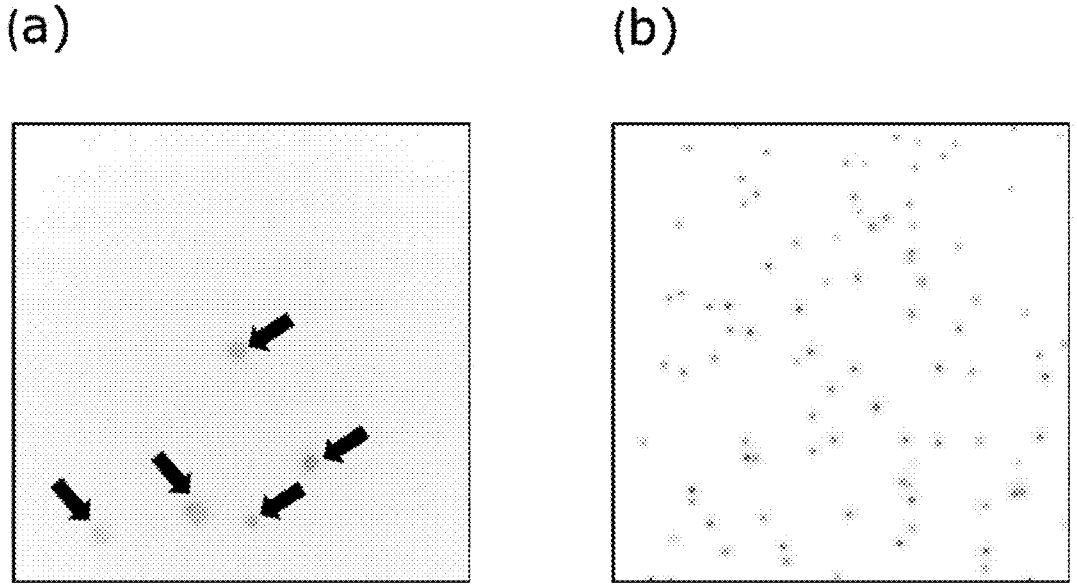

[Fig. 11]
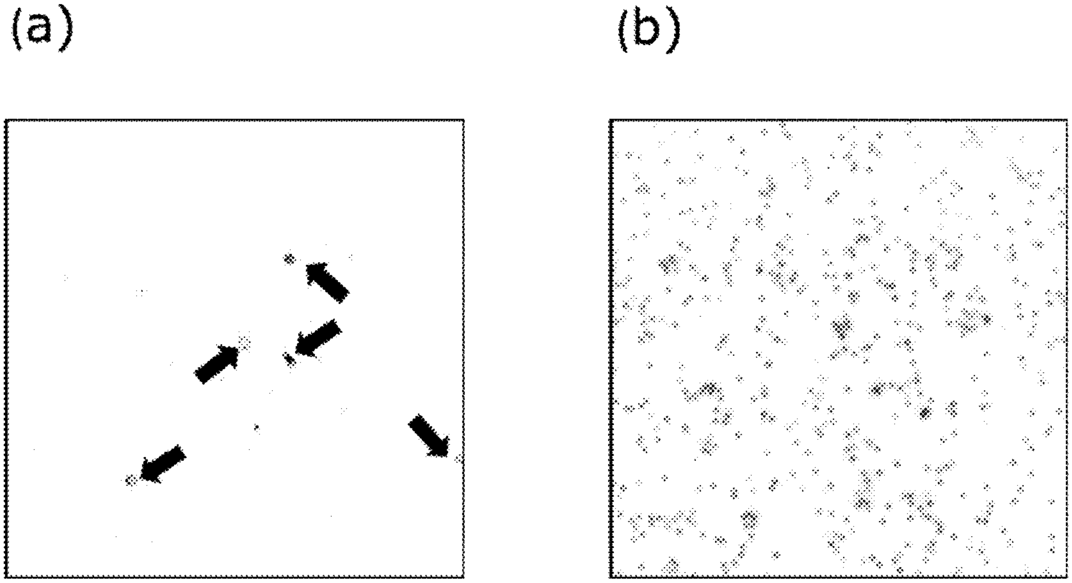

[Fig. 12]
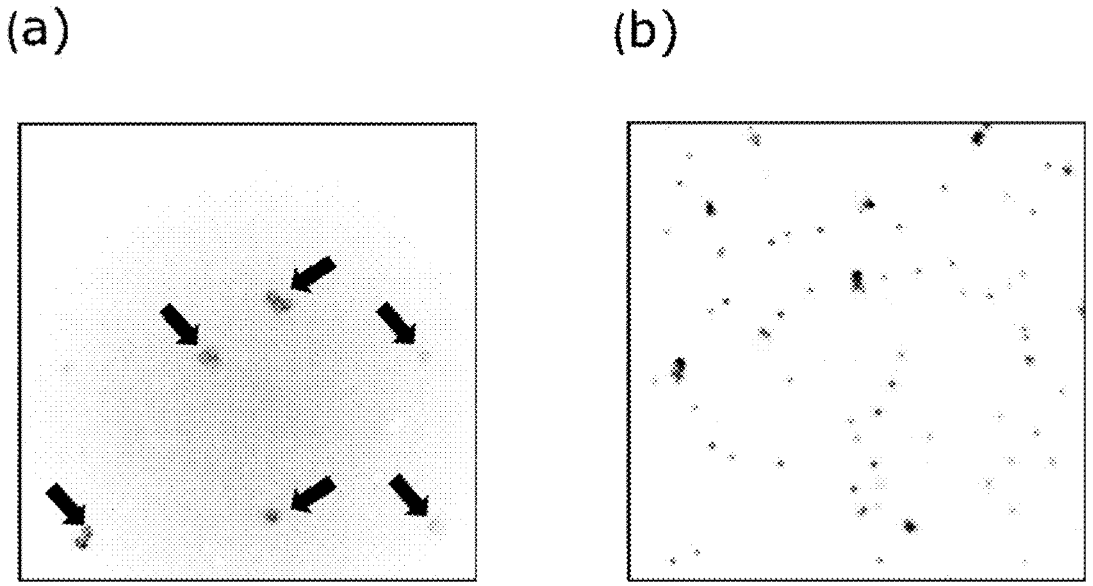

[Fig. 13]
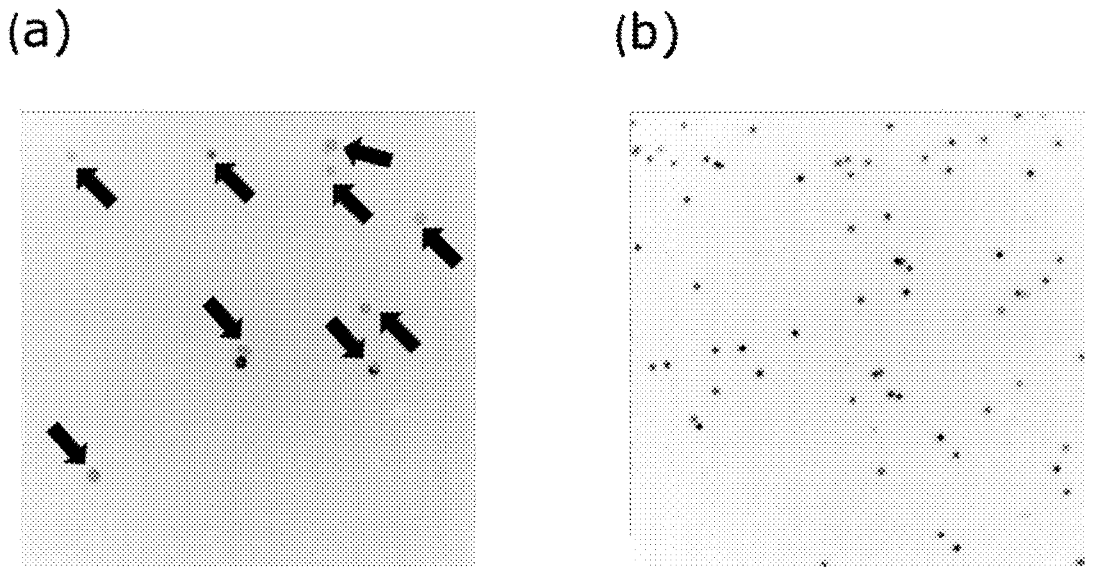

SEQUENCE LISTING

```
<160> NUMBER OF SEQ ID NOS: 12

<210> SEQ ID NO 1
<211> LENGTH: 202
<212> TYPE: PRT
<213> ORGANISM: Homo sapiens
<300> PUBLICATION INFORMATION:
<308> DATABASE ACCESSION NUMBER: GenBank/NP_055035.1
<309> DATABASE ENTRY DATE: 2016-10-07
<313> RELEVANT RESIDUES IN SEQ ID NO: (1)..(202)

<400> SEQUENCE: 1

Met Cys Tyr Gly Lys Cys Ala Arg Cys Ile Gly His Ser Leu Val Gly
1               5                   10                  15

Leu Ala Leu Leu Cys Ile Ala Ala Asn Ile Leu Leu Tyr Phe Pro Asn
            20                  25                  30

Gly Glu Thr Lys Tyr Ala Ser Glu Asn His Leu Ser Arg Phe Val Trp
        35                  40                  45

Phe Phe Ser Gly Ile Val Gly Gly Gly Leu Leu Met Leu Leu Pro Ala
    50                  55                  60

Phe Val Phe Ile Gly Leu Glu Gln Asp Asp Cys Cys Gly Cys Cys Gly
65                  70                  75                  80

His Glu Asn Cys Gly Lys Arg Cys Ala Met Leu Ser Ser Val Leu Ala
                85                  90                  95

Ala Leu Ile Gly Ile Ala Gly Ser Gly Tyr Cys Val Ile Val Ala Ala
            100                 105                 110

Leu Gly Leu Ala Glu Gly Pro Leu Cys Leu Asp Ser Leu Gly Gln Trp
        115                 120                 125

Asn Tyr Thr Phe Ala Ser Thr Glu Gly Gln Tyr Leu Leu Asp Thr Ser
    130                 135                 140

Thr Trp Ser Glu Cys Thr Glu Pro Lys His Ile Val Glu Trp Asn Val
145                 150                 155                 160

Ser Leu Phe Ser Ile Leu Leu Ala Leu Gly Gly Ile Glu Phe Ile Leu
                165                 170                 175

Cys Leu Ile Gln Val Ile Asn Gly Val Leu Gly Gly Ile Cys Gly Phe
            180                 185                 190

Cys Cys Ser His Gln Gln Gln Tyr Asp Cys
        195                 200


<210> SEQ ID NO 2
<211> LENGTH: 129
<212> TYPE: PRT
<213> ORGANISM: Homo sapiens
<300> PUBLICATION INFORMATION:
<308> DATABASE ACCESSION NUMBER: GenBank/NP_057723.1
<309> DATABASE ENTRY DATE: 2016-09-09
<313> RELEVANT RESIDUES IN SEQ ID NO: (1)..(129)
```

-continued

<400> SEQUENCE: 2

Met Ala Arg Gly Ser Leu Arg Arg Leu Leu Arg Leu Leu Val Leu Gly
1 5 10 15

Leu Trp Leu Ala Leu Leu Arg Ser Val Ala Gly Glu Gln Ala Pro Gly
20 25 30

Thr Ala Pro Cys Ser Arg Gly Ser Ser Trp Ser Ala Asp Leu Asp Lys
35 40 45

Cys Met Asp Cys Ala Ser Cys Arg Ala Arg Pro His Ser Asp Phe Cys
50 55 60

Leu Gly Cys Ala Ala Ala Pro Pro Ala Pro Phe Arg Leu Leu Trp Pro
65 70 75 80

Ile Leu Gly Gly Ala Leu Ser Leu Thr Phe Val Leu Gly Leu Leu Ser
85 90 95

Gly Phe Leu Val Trp Arg Arg Cys Arg Arg Arg Glu Lys Phe Thr Thr
100 105 110

Pro Ile Glu Glu Thr Gly Gly Glu Gly Cys Pro Ala Val Ala Leu Ile
115 120 125

Gln

<210> SEQ ID NO 3
<211> LENGTH: 310
<212> TYPE: PRT
<213> ORGANISM: Homo sapiens
<300> PUBLICATION INFORMATION:
<308> DATABASE ACCESSION NUMBER: GenBank/NP_002988.3
<309> DATABASE ENTRY DATE: 2016-09-09
<313> RELEVANT RESIDUES IN SEQ ID NO: (1)..(310)

<400> SEQUENCE: 3

Met Arg Arg Ala Ala Leu Trp Leu Trp Leu Cys Ala Leu Ala Leu Ser
1 5 10 15

Leu Gln Pro Ala Leu Pro Gln Ile Val Ala Thr Asn Leu Pro Pro Glu
20 25 30

Asp Gln Asp Gly Ser Gly Asp Asp Ser Asp Asn Phe Ser Gly Ser Gly
35 40 45

Ala Gly Ala Leu Gln Asp Ile Thr Leu Ser Gln Gln Thr Pro Ser Thr
50 55 60

Trp Lys Asp Thr Gln Leu Leu Thr Ala Ile Pro Thr Ser Pro Glu Pro
65 70 75 80

Thr Gly Leu Glu Ala Thr Ala Ala Ser Thr Ser Thr Leu Pro Ala Gly
85 90 95

Glu Gly Pro Lys Glu Gly Glu Ala Val Val Leu Pro Glu Val Glu Pro
100 105 110

Gly Leu Thr Ala Arg Glu Gln Glu Ala Thr Pro Arg Pro Arg Glu Thr
115 120 125

Thr Gln Leu Pro Thr Thr His Gln Ala Ser Thr Thr Thr Ala Thr Thr
130 135 140

Ala Gln Glu Pro Ala Thr Ser His Pro His Arg Asp Met Gln Pro Gly
145 150 155 160

His His Glu Thr Ser Thr Pro Ala Gly Pro Ser Gln Ala Asp Leu His
165 170 175

Thr Pro His Thr Glu Asp Gly Gly Pro Ser Ala Thr Glu Arg Ala Ala
180 185 190

Glu Asp Gly Ala Ser Ser Gln Leu Pro Ala Ala Glu Gly Ser Gly Glu
195 200 205

```
Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310


<210> SEQ ID NO 4
<211> LENGTH: 295
<212> TYPE: PRT
<213> ORGANISM: Homo sapiens
<300> PUBLICATION INFORMATION:
<308> DATABASE ACCESSION NUMBER: GenBank/NP_001984.1
<309> DATABASE ENTRY DATE: 2016-10-07
<313> RELEVANT RESIDUES IN SEQ ID NO: (1)..(295)

<400> SEQUENCE: 4

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240
```

```
Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
    290                 295


<210> SEQ ID NO 5
<211> LENGTH: 976
<212> TYPE: PRT
<213> ORGANISM: Homo sapiens
<300> PUBLICATION INFORMATION:
<308> DATABASE ACCESSION NUMBER: GenBank/NP_004422.2
<309> DATABASE ENTRY DATE: 2016-10-09
<313> RELEVANT RESIDUES IN SEQ ID NO: (1)..(976)

<400> SEQUENCE: 5

Met Glu Leu Gln Ala Ala Arg Ala Cys Phe Ala Leu Leu Trp Gly Cys
1               5                   10                  15

Ala Leu Ala Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
```

-continued

```
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720
```

```
Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
    930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975
```

<210> SEQ ID NO 6
<211> LENGTH: 1181
<212> TYPE: PRT
<213> ORGANISM: Homo sapiens
<300> PUBLICATION INFORMATION:
<308> DATABASE ACCESSION NUMBER: GenBank/NP_002194.2
<309> DATABASE ENTRY DATE: 2016-02-21
<313> RELEVANT RESIDUES IN SEQ ID NO: (1)..(1181)

<400> SEQUENCE: 6

```
Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
            20                  25                  30

Gly Leu Pro Glu Ala Lys Ile Phe Ser Gly Pro Ser Ser Glu Gln Phe
        35                  40                  45

Gly Tyr Ala Val Gln Gln Phe Ile Asn Pro Lys Gly Asn Trp Leu Leu
    50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
                85                  90                  95
```

-continued

```
Leu Gln Thr Ser Thr Ser Ile Pro Asn Val Thr Glu Met Lys Thr Asn
            100                 105                 110

Met Ser Leu Gly Leu Ile Leu Thr Arg Asn Met Gly Thr Gly Gly Phe
        115                 120                 125

Leu Thr Cys Gly Pro Leu Trp Ala Gln Gln Cys Gly Asn Gln Tyr Tyr
    130                 135                 140

Thr Thr Gly Val Cys Ser Asp Ile Ser Pro Asp Phe Gln Leu Ser Ala
145                 150                 155                 160

Ser Phe Ser Pro Ala Thr Gln Pro Cys Pro Ser Leu Ile Asp Val Val
                165                 170                 175

Val Val Cys Asp Glu Ser Asn Ser Ile Tyr Pro Trp Asp Ala Val Lys
            180                 185                 190

Asn Phe Leu Glu Lys Phe Val Gln Gly Leu Asp Ile Gly Pro Thr Lys
        195                 200                 205

Thr Gln Val Gly Leu Ile Gln Tyr Ala Asn Asn Pro Arg Val Val Phe
    210                 215                 220

Asn Leu Asn Thr Tyr Lys Thr Lys Glu Glu Met Ile Val Ala Thr Ser
225                 230                 235                 240

Gln Thr Ser Gln Tyr Gly Gly Asp Leu Thr Asn Thr Phe Gly Ala Ile
                245                 250                 255

Gln Tyr Ala Arg Lys Tyr Ala Tyr Ser Ala Ala Ser Gly Gly Arg Arg
            260                 265                 270

Ser Ala Thr Lys Val Met Val Val Val Thr Asp Gly Glu Ser His Asp
        275                 280                 285

Gly Ser Met Leu Lys Ala Val Ile Asp Gln Cys Asn His Asp Asn Ile
    290                 295                 300

Leu Arg Phe Gly Ile Ala Val Leu Gly Tyr Leu Asn Arg Asn Ala Leu
305                 310                 315                 320

Asp Thr Lys Asn Leu Ile Lys Glu Ile Lys Ala Ile Ala Ser Ile Pro
                325                 330                 335

Thr Glu Arg Tyr Phe Phe Asn Val Ser Asp Glu Ala Ala Leu Leu Glu
            340                 345                 350

Lys Ala Gly Thr Leu Gly Glu Gln Ile Phe Ser Ile Glu Gly Thr Val
        355                 360                 365

Gln Gly Gly Asp Asn Phe Gln Met Glu Met Ser Gln Val Gly Phe Ser
    370                 375                 380

Ala Asp Tyr Ser Ser Gln Asn Asp Ile Leu Met Leu Gly Ala Val Gly
385                 390                 395                 400

Ala Phe Gly Trp Ser Gly Thr Ile Val Gln Lys Thr Ser His Gly His
                405                 410                 415

Leu Ile Phe Pro Lys Gln Ala Phe Asp Gln Ile Leu Gln Asp Arg Asn
            420                 425                 430

His Ser Ser Tyr Leu Gly Tyr Ser Val Ala Ala Ile Ser Thr Gly Glu
        435                 440                 445

Ser Thr His Phe Val Ala Gly Ala Pro Arg Ala Asn Tyr Thr Gly Gln
    450                 455                 460

Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
                485                 490                 495

Ser Val Asp Val Asp Lys Asp Thr Ile Thr Asp Val Leu Leu Val Gly
            500                 505                 510

Ala Pro Met Tyr Met Ser Asp Leu Lys Lys Glu Glu Gly Arg Val Tyr
```

-continued

```
        515                 520                 525

Leu Phe Thr Ile Lys Glu Gly Ile Leu Gly Gln His Gln Phe Leu Glu
    530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
    610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
        675                 680                 685

Lys Gln Asn Asn Gln Val Ala Ile Val Tyr Asn Ile Thr Leu Asp Ala
    690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
        755                 760                 765

Pro Ala Leu Glu Ala Tyr Ser Glu Thr Ala Lys Val Phe Ser Ile Pro
    770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
        835                 840                 845

Leu Phe Phe Ala Ser Phe Ser Leu Pro Val Asp Gly Thr Glu Val Thr
    850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
                885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
        915                 920                 925

Lys Ile Pro Leu Leu Tyr Asp Ala Glu Ile His Leu Thr Arg Ser Thr
    930                 935                 940
```

-continued

```
Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
                965                 970                 975

Val Thr Thr Gly Ser Val Pro Val Ser Met Ala Thr Val Ile Ile His
            980                 985                 990

Ile Pro Gln Tyr Thr Lys Glu Lys Asn Pro Leu Met Tyr Leu Thr Gly
        995                 1000                1005

Val Gln Thr Asp Lys Ala Gly Asp Ile Ser Cys Asn Ala Asp Ile Asn
    1010                1015                1020

Pro Leu Lys Ile Gly Gln Thr Ser Ser Ser Val Ser Phe Lys Ser Glu
1025                1030                1035                1040

Asn Phe Arg His Thr Lys Glu Leu Asn Cys Arg Thr Ala Ser Cys Ser
                1045                1050                1055

Asn Val Thr Cys Trp Leu Lys Asp Val His Met Lys Gly Glu Tyr Phe
            1060                1065                1070

Val Asn Val Thr Thr Arg Ile Trp Asn Gly Thr Phe Ala Ser Ser Thr
        1075                1080                1085

Phe Gln Thr Val Gln Leu Thr Ala Ala Ala Glu Ile Asn Thr Tyr Asn
    1090                1095                1100

Pro Glu Ile Tyr Val Ile Glu Asp Asn Thr Val Thr Ile Pro Leu Met
1105                1110                1115                1120

Ile Met Lys Pro Asp Glu Lys Ala Glu Val Pro Thr Gly Val Ile Ile
                1125                1130                1135

Gly Ser Ile Ile Ala Gly Ile Leu Leu Leu Leu Ala Leu Val Ala Ile
            1140                1145                1150

Leu Trp Lys Leu Gly Phe Phe Lys Arg Lys Tyr Glu Lys Met Thr Lys
        1155                1160                1165

Asn Pro Asp Glu Ile Asp Glu Thr Thr Glu Leu Ser Ser
    1170                1175                1180


<210> SEQ ID NO 7
<211> LENGTH: 1712
<212> TYPE: DNA
<213> ORGANISM: Homo sapiens
<300> PUBLICATION INFORMATION:
<308> DATABASE ACCESSION NUMBER: GenBank/NM_014220.2
<309> DATABASE ENTRY DATE: 2016-10-07
<313> RELEVANT RESIDUES IN SEQ ID NO: (1)..(1712)

<400> SEQUENCE: 7

aagggcggga cattcccccct gcctcttcgc accacagcca gagcctgcca ttaggaccaa     60

tgaaagcaaa gtacctcatc ccctcagtga ctaagaatcg cagtatttaa gaggtagcag    120

gaatgggctg agagtggtgt ttgctttctc caccagaagg gcacactttc atctaatttg    180

gggtatcact gagctgaaga caaagagaag ggggagaaaa cctagcagac caccatgtgc    240

tatgggaagt gtgcacgatg catcggacat tctctggtgg ggctcgccct cctgtgcatc    300

gcggctaata ttttgcttta ctttcccaat ggggaaacaa agtatgcctc cgaaaaccac    360

ctcagccgct tcgtgtggtt cttttctggc atcgtaggag gtggcctgct gatgctcctg    420

ccagcatttg tcttcattgg gctggaacag gatgactgct gtggctgctg tggccatgaa    480

aactgtggca aacgatgtgc gatgctttct tctgtattgg ctgctctcat tggaattgca    540

ggatctggct actgtgtcat tgtggcagcc cttggcttag cagaaggacc actatgtctt    600

gattccctcg gccagtggaa ctacaccttt gccagcactg agggccagta ccttctggat    660
```

```
acctccacat ggtccgagtg cactgaaccc aagcacattg tggaatggaa tgtatctctg    720
ttttctatcc tcttggctct tggtggaatt gaattcatct tgtgtcttat tcaagtaata    780
aatggagtgc ttggaggcat atgtggcttt tgctgctctc accaacagca atatgactgc    840
taaaagaacc aacccaggac agagccacaa tcttcctcta tttcattgta atttatatat    900
ttcacttgta ttcatttgta aaactttgta ttagtgtaac atactcccca cagtctactt    960
ttacaaacgc ctgtaaagac tggcatcttc acaggatgtc agtgtttaaa tttagtaaac   1020
ttcttttttg tttgtttatt tgtttttgtt ttttttaag gaatgaggaa acaaaccacc   1080
ctctgggggt aatttacaga ctgagtgaca gtactcagta tatctgagat aaactctata   1140
atgttttgga taaaaataac attccaatca ctattgtata tatgtgcatg tattttttaa   1200
attaaagatg tctagttgct ttttataaga ccaagaagga gaaaatccga caacctggaa   1260
agatttttgt tttcactgct tgtatgatgt ttcccattca tacacctata aatctctaac   1320
aagaggccct ttgaactgcc ttgtgttctg tgagaaacaa atatttactt agagtggaag   1380
gactgattga gaatgttcca atccaaatga atgcatcaca acttacaatg ctgctcattg   1440
ttgtgagtac tatgagattc aaatttttct aacatatgga aagccttttg tcctccaaag   1500
atgagtacta gggatcatgt gtttaaaaaa agaaaggcta cgatgactgg gcaagaagaa   1560
agatgggaaa ctgaataaag cagttgatca gcatcattgg aacatgggga cgagtgacgg   1620
caggaggacc acgaggaaat accctcaaaa ctaacttgtt tacaacaaaa taaagtattc   1680
actaccatgt taaaaaaaaa aaaaaaaaaa aa                                 1712
```

<210> SEQ ID NO 8
<211> LENGTH: 1048
<212> TYPE: DNA
<213> ORGANISM: Homo sapiens
<300> PUBLICATION INFORMATION:
<308> DATABASE ACCESSION NUMBER: GenBank/NM_016639.2
<309> DATABASE ENTRY DATE: 2016-09-09
<313> RELEVANT RESIDUES IN SEQ ID NO: (1)..(1048)

<400> SEQUENCE: 8

```
aaggcggggg cgggggcggg gcggcggccg tgggtccctg ccggccggcg gcgggcgcag     60
acagcggcgg gcgcaggacg tgcactatgg ctcggggctc gctgcgccgg ttgctgcggc    120
tcctcgtgct ggggctctgg ctggcgttgc tgcgctccgt ggccggggag caagcgccag    180
gcaccgcccc ctgctcccgc ggcagctcct ggagcgcgga cctggacaag tgcatggact    240
gcgcgtcttg cagggcgcga ccgcacagcg acttctgcct gggctgcgct gcagcacctc    300
ctgccccctt ccggctgctt tggcccatcc ttgggggcgc tctgagcctg accttcgtgc    360
tggggctgct ttctggcttt ttggtctgga gacgatgccg caggagagag aagttcacca    420
cccccataga ggagaccggc ggagagggct gcccagctgt ggcgctgatc cagtgacaat    480
gtgccccctg ccagccgggg ctcgcccact catcattcat tcatccattc tagagccagt    540
ctctgcctcc cagacgcggc gggagccaag ctcctccaac cacaaggggg gtgggggcg     600
gtgaatcacc tctgaggcct gggcccaggg ttcaggggaa ccttccaagg tgtctggttg    660
ccctgcctct ggctccagaa cagaaaggga gcctcacgct ggctcacaca aaacagctga    720
cactgactaa ggaactgcag catttgcaca ggggaggggg gtgccctcct tcctagaggc    780
cctgggggcc aggctgactt ggggggcaga cttgacacta ggccccactc actcagatgt    840
cctgaaattc caccacgggg gtcaccctgg ggggttaggg acctattttt aacactaggg    900
```

-continued ggctggccca ctaggagggc tggccctaag atacagaccc ccccaactcc ccaaagcggg 960
gaggagatat ttattttggg gagagtttgg aggggaggga gaatttatta ataaaagaat 1020
ctttaacttt aaaaaaaaaa aaaaaaaa 1048

<210> SEQ ID NO 9
<211> LENGTH: 3309
<212> TYPE: DNA
<213> ORGANISM: Homo sapiens
<300> PUBLICATION INFORMATION:
<308> DATABASE ACCESSION NUMBER: GenBank/NM_001006946.1
<309> DATABASE ENTRY DATE: 2016-09-09
<313> RELEVANT RESIDUES IN SEQ ID NO: (1)..(3309)

<400> SEQUENCE: 9
ttcagcccct ctcccgggct gcgcctccgc actccgggcc cgggcagaag ggggtgcgcc 60
tcggccccac cacccaggga gcagccgagc tgaaaggccg ggaaccgcgg cttgcgggga 120
ccacagctcc cgaaagcgac gttcggccac cggaggagcg ggagccaagc aggcggagct 180
cggcgggaga ggtgcgggcc gaatccgagc cgagcggaga ggaatccggc agtagagagc 240
ggactccagc cggcggaccc tgcagccctc gcctgggaca gcggcgcgct gggcaggcgc 300
ccaagagagc atcgagcagc ggaacccgcg aagccggccc gcagccgcga cccgcgcagc 360
ctgccgctct cccgccgccg gtccgggcag catgaggcgc gcggcgctct ggctctggct 420
gtgcgcgctg gcgctgagcc tgcagccggc cctgccgcaa attgtggcta ctaatttgcc 480
ccctgaagat caagatggct ctggggatga ctctgacaac ttctccggct caggtgcagg 540
tgctttgcaa gatatcacct tgtcacagca gaccccctcc acttggaagg acacgcagct 600
cctgacggct attcccacgt ctccagaacc caccggcctg gaggctacag ctgcctccac 660
ctccaccctg ccggctggag aggggcccaa ggagggagag gctgtagtcc tgccagaagt 720
ggagcctggc ctcaccgccc gggagcagga ggccaccccc cgacccaggg agaccacaca 780
gctcccgacc actcatcagg cctcaacgac cacagccacc acggcccagg agcccgccac 840
ctcccacccc cacagggaca tgcagcctgg ccaccatgag acctcaaccc ctgcaggacc 900
cagccaagct gaccttcaca ctccccacac agaggatgga ggtccttctg ccaccgagag 960
ggctgctgag gatggagcct ccagtcagct cccagcagca gagggctctg gggagcagga 1020
cttcaccttt gaaacctcgg gggagaatac ggctgtagtg gccgtggagc ctgaccgccg 1080
gaaccagtcc ccagtggatc agggggccac gggggcctca cagggcctcc tggacaggaa 1140
agaggtgctg ggaggggtca ttgccggagg cctcgtgggg ctcatctttg ctgtgtgcct 1200
ggtgggtttc atgctgtacc gcatgaagaa gaaggacgaa ggcagctact ccttggagga 1260
gccgaaacaa gccaacggcg gggcctacca gaagcccacc aaacaggagg aattctatgc 1320
ctgacgcggg agccatgcgc cccctccgcc ctgccactca ctaggccccc acttgcctct 1380
tccttgaaga actgcaggcc ctggcctccc ctgccaccag gccacctccc cagcattcca 1440
gcccctctgg tcgctcctgc ccacggagtc gtggggtgtg ctgggagctc cactctgctt 1500
ctctgacttc tgcctggaga cttagggcac caggggtttc tcgcatagga cctttccacc 1560
acagccagca cctggcatcg caccattctg actcggtttc tccaaactga agcagcctct 1620
ccccaggtcc agctctggag gggagggga tccgactgct ttggacctaa atggcctcat 1680
gtggctggaa gatcctgcgg gtggggcttg gggctcacac acctgtagca cttactggta 1740
ggaccaagca tcttgggggg gtggccgctg agtggcaggg gacaggagtc cactttgttt 1800
cgtggggagg tctaatctag atatcgactt gtttttgcac atgtttcctc tagttctttg 1860

-continued

```
ttcatagccc agtagacctt gttacttctg aggtaagtta agtaagttga ttcggtatcc   1920

ccccatcttg cttccctaat ctatggtcgg gagacagcat cagggttaag aagacttttt   1980

tttttttttt ttaaactagg agaaccaaat ctggaagcca aaatgtaggc ttagtttgtg   2040

tgttgtctct tgagtttgtc gctcatgtgt gcaacagggt atggactatc tgtctggtgg   2100

ccccgtttct ggtggtctgt tggcaggctg gccagtccag gctgccgtgg ggccgccgcc   2160

tctttcaagc agtcgtgcct gtgtccatgc gctcagggcc atgctgaggc ctgggccgct   2220

gccacgttgg agaagcccgt gtgagaagtg aatgctggga ctcagccttc agacagagag   2280

gactgtaggg agggcggcag gggcctggag atcctcctgc agaccacgcc cgtcctgcct   2340

gtggcgccgt ctccaggggc tgcttcctcc tggaaattga cgaggggtgt cttgggcaga   2400

gctggctctg agcgcctcca tccaaggcca ggttctccgt tagctcctgt ggccccaccc   2460

tgggccctgg gctggaatca ggaatatttt ccaaagagtg atagtctttt gcttttggca   2520

aaactctact taatccaatg ggtttttccc tgtacagtag attttccaaa tgtaataaac   2580

tttaatataa agtagtcctg tgaatgccac tgccttcgct tcttgcctct gtgctgtgtg   2640

tgacgtgacc ggacttttct gcaaacacca acatgttggg aaacttggct cgaatctctg   2700

tgccttcgtc tttcccatgg ggagggattc tggttccagg gtccctctgt gtatttgctt   2760

ttttgttttg gctgaaattc tcctggaggt cggtaggttc agccaaggtt ttataaggct   2820

gatgtcaatt tctgtgttgc caagctccaa gccccatctt ctaaatggca aaggaaggtg   2880

gatggcccca gcacagcttg acctgaggct gtggtcacag cggaggtgtg gagccgaggc   2940

ctaccccgca gacaccttgg acatcctcct cccacccggc tgcagaggcc agaggccccc   3000

agcccagggc tcctgcactt acttgcttat ttgacaacgt ttcagcgact ccgttggcca   3060

ctccgagagg tgggccagtc tgtggatcag agatgcacca ccaagccaag ggaacctgtg   3120

tccggtattc gatactgcga ctttctgcct ggagtgtatg actgcacatg actcgggggt   3180

ggggaaaggg gtcggctgac catgctcatc tgctggtccg tgggacggtg cccaagccag   3240

aggctgggtt catttgtgta acgacaataa acggtacttg tcatttcggg caaaaaaaaa   3300

aaaaaaaaa                                                           3309
```

<210> SEQ ID NO 10
<211> LENGTH: 2393
<212> TYPE: DNA
<213> ORGANISM: Homo sapiens
<300> PUBLICATION INFORMATION:
<308> DATABASE ACCESSION NUMBER: GenBank/NM_001993.4
<309> DATABASE ENTRY DATE: 2016-10-07
<313> RELEVANT RESIDUES IN SEQ ID NO: (1)..(2393)

<400> SEQUENCE: 10

```
ggagtcggga ggagcggcgg gggcgggcgc cgggggcggg cagaggcgcg ggagagcgcg     60

ccgccggccc tttatagcgc gcggggcacc ggctccccaa gactgcgagc tccccgcacc    120

ccctcgcact ccctctggcc ggcccagggc gccttcagcc caacctcccc agccccacgg    180

gcgccacgga acccgctcga tctcgccgcc aactggtaga catggagacc cctgcctggc    240

cccgggtccc gcgccccgag accgccgtcg ctcggacgct cctgctcggc tgggtcttcg    300

cccaggtggc cggcgcttca ggcactacaa atactgtggc agcatataat ttaacttgga    360

aatcaactaa tttcaagaca attttggagt gggaacccaa acccgtcaat caagtctaca    420

ctgttcaaat aagcactaag tcaggagatt ggaaaagcaa atgcttttac acaacagaca    480
```

```
cagagtgtga cctcaccgac gagattgtga aggatgtgaa gcagacgtac ttggcacggg    540

tcttctccta cccggcaggg aatgtggaga gcaccggttc tgctggggag cctctgtatg    600

agaactcccc agagttcaca ccttacctgg agacaaacct cggacagcca acaattcaga    660

gttttgaaca ggtgggaaca aaagtgaatg tgaccgtaga agatgaacgg actttagtca    720

gaaggaacaa cactttccta agcctccggg atgtttttgg caaggactta atttatacac    780

tttattattg gaaatcttca agttcaggaa agaaaacagc caaaacaaac actaatgagt    840

ttttgattga tgtggataaa ggagaaaact actgtttcag tgttcaagca gtgattccct    900

cccgaacagt taaccggaag agtacagaca gcccggtaga gtgtatgggc caggagaaag    960

gggaattcag agaaatattc tacatcattg gagctgtggt atttgtggtc atcatccttg   1020

tcatcatcct ggctatatct ctacacaagt gtagaaaggc aggagtgggg cagagctgga   1080

aggagaactc cccactgaat gtttcataaa ggaagcactg ttggagctac tgcaaatgct   1140

atattgcact gtgaccgaga acttttaaga ggatagaata catggaaacg caaatgagta   1200

tttcggagca tgaagaccct ggagttcaaa aaactcttga tatgacctgt tattaccatt   1260

agcattctgg ttttgacatc agcattagtc actttgaaat gtaacgaatg gtactacaac   1320

caattccaag ttttaatttt taacaccatg gcaccttttg cacataacat gctttagatt   1380

atatattccg cactcaagga gtaaccaggt cgtccaagca aaaacaaatg ggaaaatgtc   1440

ttaaaaaatc ctgggtggac ttttgaaaag cttttttttt tttttttttt tttttgagac   1500

ggagtcttgc tctgttgccc aggctggagt gcagtagcac gatctcggct cactgcaccc   1560

tccgtctctc gggttcaagc aattgtctgc ctcagcctcc cgagtagctg ggattacagg   1620

tgcgcactac cacgccaagc taatttttgt atttttagt agagatgggg tttcaccatc    1680

ttggccaggc tggtcttgaa ttcctgacct caggtgatcc acccaccttg gcctcccaaa   1740

gtgctagtat tatgggcgtg aaccaccatg cccagccgaa aagcttttga ggggctgact   1800

tcaatccatg taggaaagta aaatggaagg aaattgggtg catttctagg acttttctaa   1860

catatgtcta taatatagtg tttaggttct tttttttttc aggaatacat ttggaaattc   1920

aaaacaattg gcaaactttg tattaatgtg ttaagtgcag gagacattgg tattctgggc   1980

accttcctaa tatgctttac aatctgcact ttaactgact taagtggcat taaacatttg   2040

agagctaact atatttttat aagactacta tacaaactac agagtttatg atttaaggta   2100

cttaaagctt ctatggttga cattgtatat ataatttttt aaaaaggttt tctatatggg   2160

gattttctat ttatgtaggt aatattgttc tatttgtata tattgagata atttatttaa   2220

tatactttaa ataaaggtga ctgggaattg ttactgttgt acttattcta tcttccattt   2280

attatttatg tacaatttgg tgtttgtatt agctctacta cagtaaatga ctgtaaaatt   2340

gtcagtggct tacaacaacg tatctttttc gcttataata cattttggtg act          2393
```

<210> SEQ ID NO 11
<211> LENGTH: 3970
<212> TYPE: DNA
<213> ORGANISM: Homo sapiens
<300> PUBLICATION INFORMATION:
<308> DATABASE ACCESSION NUMBER: GenBank/NM_004431.3
<309> DATABASE ENTRY DATE: 2015-03-15
<313> RELEVANT RESIDUES IN SEQ ID NO: (1)..(3970)

<400> SEQUENCE: 11

```
ggttctcacc caacttccat taaggactcg gggcaggagg ggcagaagtt gcgcgcaggc     60

cggcgggcgg gagcggacac cgaggccggc gtgcaggcgt gcgggtgtgc gggagccggg    120
```

-continued

```
ctcgggggga tcggaccgag agcgagaagc gcggcatgga gctccaggca gcccgcgcct    180
gcttcgccct gctgtggggc tgtgcgctgg ccgcggccgc ggcggcgcag ggcaaggaag    240
tggtactgct ggactttgct gcagctggag gggagctcgg ctggctcaca cacccgtatg    300
gcaaagggtg ggacctgatg cagaacatca tgaatgacat gccgatctac atgtactccg    360
tgtgcaacgt gatgtctggc gaccaggaca actggctccg caccaactgg gtgtaccgag    420
gagaggctga gcgtatcttc attgagctca agtttactgt acgtgactgc aacagcttcc    480
ctggtggcgc cagctcctgc aaggagactt tcaacctcta ctatgccgag tcggacctgg    540
actacggcac caacttccag aagcgcctgt tcaccaagat tgacaccatt gcgcccgatg    600
agatcaccgt cagcagcgac ttcgaggcac gccacgtgaa gctgaacgtg gaggagcgct    660
ccgtggggcc gctcacccgc aaaggcttct acctggcctt ccaggatatc ggtgcctgtg    720
tggcgctgct ctccgtccgt gtctactaca agaagtgccc cgagctgctg cagggcctgg    780
cccacttccc tgagaccatc gccggctctg atgcaccttc cctggccact gtggccggca    840
cctgtgtgga ccatgccgtg gtgccaccgg ggggtgaaga gccccgtatg cactgtgcag    900
tggatggcga gtggctggtg cccattgggc agtgcctgtg ccaggcaggc tacgagaagg    960
tggaggatgc ctgccaggcc tgctcgcctg gatttttaa gtttgaggca tctgagagcc    1020
cctgcttgga gtgccctgag cacacgctgc catcccctga gggtgccacc tcctgcgagt    1080
gtgaggaagg cttcttccgg gcacctcagg acccagcgtc gatgccttgc acacgacccc    1140
cctccgcccc acactacctc acagccgtgg gcatgggtgc caaggtggag ctgcgctgga    1200
cgccccctca ggacagcggg ggccgcgagg acattgtcta cagcgtcacc tgcgaacagt    1260
gctggcccga gtctggggaa tgcgggccgt gtgaggccag tgtgcgctac tcggagcctc    1320
ctcacggact gacccgcacc agtgtgacag tgagcgacct ggagccccac atgaactaca    1380
ccttcaccgt ggaggcccgc aatggcgtct caggcctggt aaccagccgc agcttccgta    1440
ctgccagtgt cagcatcaac cagacagagc cccccaaggt gaggctggag ggccgcagca    1500
ccacctcgct tagcgtctcc tggagcatcc ccccgccgca gcagagccga gtgtggaagt    1560
acgaggtcac ttaccgcaag aagggagact ccaacagcta caatgtgcgc cgcaccgagg    1620
gtttctccgt gaccctggac gacctggccc cagacaccac ctacctggtc caggtgcagg    1680
cactgacgca ggagggccag ggggccggca gcaaggtgca cgaattccag acgctgtccc    1740
cggagggatc tggcaacttg gcggtgattg gcggcgtggc tgtcggtgtg gtcctgcttc    1800
tggtgctggc aggagttggc ttctttatcc accgcaggag gaagaaccag cgtgcccgcc    1860
agtccccgga ggacgtttac ttctccaagt cagaacaact gaagcccctg aagacatacg    1920
tggaccccca cacatatgag gaccccaacc aggctgtgtt gaagttcact accgagatcc    1980
atccatcctg tgtcactcgg cagaaggtga tcggagcagg agagtttggg gaggtgtaca    2040
agggcatgct gaagacatcc tcggggaaga aggaggtgcc ggtggccatc aagacgctga    2100
aagccggcta cacagagaag cagcgagtgg acttcctcgg cgaggccggc atcatgggcc    2160
agttcagcca ccacaacatc atccgcctag agggcgtcat ctccaaatac aagcccatga    2220
tgatcatcac tgagtacatg gagaatgggg ccctggacaa gttccttcgg gagaaggatg    2280
gcgagttcag cgtgctgcag ctggtgggca tgctgcgggg catcgcagct ggcatgaagt    2340
acctggccaa catgaactat gtgcaccgtg acctggctgc ccgcaacatc ctcgtcaaca    2400
gcaacctggt ctgcaaggtg tctgactttg gcctgtcccg cgtgctggag gacgaccccg    2460
```

-continued

```
aggccaccta caccaccagt ggcggcaaga tccccatccg ctggaccgcc ccggaggcca   2520
tttcctaccg gaagttcacc tctgccagcg acgtgtggag ctttggcatt gtcatgtggg   2580
aggtgatgac ctatggcgag cggccctact gggagttgtc caaccacgag gtgatgaaag   2640
ccatcaatga tggcttccgg ctccccacac ccatggactg cccctccgcc atctaccagc   2700
tcatgatgca gtgctggcag caggagcgtg cccgccgccc caagttcgct gacatcgtca   2760
gcatcctgga caagctcatt cgtgcccctg actccctcaa gaccctggct gactttgacc   2820
cccgcgtgtc tatccggctc cccagcacga gcggctcgga gggggtgccc ttccgcacgg   2880
tgtccgagtg gctggagtcc atcaagatgc agcagtatac ggagcacttc atggcggccg   2940
gctacactgc catcgagaag gtggtgcaga tgaccaacga cgacatcaag aggattgggg   3000
tgcggctgcc cggccaccag aagcgcatcg cctacagcct gctgggactc aaggaccagg   3060
tgaacactgt ggggatcccc atctgagcct cgacagggcc tggagcccca tcggccaaga   3120
atacttgaag aaacagagtg gcctccctgc tgtgccatgc tgggccactg gggactttat   3180
ttatttctag ttctttcctc cccctgcaac ttccgctgag ggtctcgga tgacaccctg   3240
gcctgaactg aggagatgac cagggatgct gggctgggcc ctctttccct gcgagacgca   3300
cacagctgag cacttagcag gcaccgccac gtcccagcat ccctggagca ggagccccgc   3360
cacagccttc ggacagacat atgggatatt cccaagccga ccttccctcc gccttctccc   3420
acatgaggcc atctcaggag atggagggct tggcccagcg ccaagtaaac agggtacctc   3480
aagccccatt tcctcacact aagagggcag actgtgaact tgactgggtg agacccaaag   3540
cggtccctgt ccctctagtg ccttctttag accctcgggc cccatcctca tccctgactg   3600
gccaaaccct tgctttcctg ggcctttgca agatgcttgg ttgtgttgag gtttttaaat   3660
atatattttg tactttgtgg agagaatgtg tgtgtgtggc agggggcccc gccagggctg   3720
gggacagagg gtgtcaaaca ttcgtgagct ggggactcag ggaccggtgc tgcaggagtg   3780
tcctgcccat gccccagtcg gccccatctc tcatcctttt ggataagttt ctattctgtc   3840
agtgttaaag attttgtttt gttggacatt tttttcgaat cttaatttat tattttttt   3900
atatttattg ttagaaaatg acttatttct gctctggaat aaagttgcag atgattcaaa   3960
ccgaaaaaaa                                                          3970
```

<210> SEQ ID NO 12
<211> LENGTH: 7878
<212> TYPE: DNA
<213> ORGANISM: Homo sapiens
<300> PUBLICATION INFORMATION:
<308> DATABASE ACCESSION NUMBER: GenBank/NM_002203.3
<309> DATABASE ENTRY DATE: 2016-02-21
<313> RELEVANT RESIDUES IN SEQ ID NO: (1)..(7878)

<400> SEQUENCE: 12

```
ttttccctgc tctcaccggg cgggggagag aagccctctg gacagcttct agagtgtgca     60
ggttctcgta tccctcggcc aagggtatcc tctgcaaacc tctgcaaacc cagcgcaact    120
acggtccccc ggtcagaccc aggatggggc cagaacggac aggggccgcg ccgctgccgc    180
tgctgctggt gttagcgctc agtcaaggca ttttaaattg ttgtttggcc tacaatgttg    240
gtctcccaga agcaaaaata ttttccggtc cttcaagtga acagtttggc tatgcagtgc    300
agcagtttat aaatccaaaa ggcaactggt tactggttgg ttcaccctgg agtggctttc    360
ctgagaaccg aatgggagat gtgtataaat gtcctgttga cctatccact gccacatgtg    420
aaaaactaaa tttgcaaact tcaacaagca ttccaaatgt tactgagatg aaaaccaaca    480
```

```
tgagcctcgg cttgatcctc accaggaaca tgggaactgg aggttttctc acatgtggtc    540
ctctgtgggc acagcaatgt gggaatcagt attacacaac gggtgtgtgt tctgacatca    600
gtcctgattt tcagctctca gccagcttct cacctgcaac tcagccctgc ccttccctca    660
tagatgttgt ggttgtgtgt gatgaatcaa atagtattta tccttgggat gcagtaaaga    720
atttttttgga aaaatttgta caaggcctgg atataggccc cacaaagaca caggtggggt    780
taattcagta tgccaataat ccaagagttg tgtttaactt gaacacatat aaaaccaaag    840
aagaaatgat tgtagcaaca tcccagacat cccaatatgg tggggacctc acaaacacat    900
tcggagcaat tcaatatgca agaaaatatg cttattcagc agcttctggt gggcgacgaa    960
gtgctacgaa agtaatggta gttgtaactg acggtgaatc acatgatggt tcaatgttga   1020
aagctgtgat tgatcaatgc aaccatgaca atatactgag gtttggcata gcagttcttg   1080
ggtacttaaa cagaaacgcc cttgatacta aaaatttaat aaaagaaata aaagcaatcg   1140
ctagtattcc aacagaaaga tactttttca atgtgtctga tgaagcagct ctactagaaa   1200
aggctgggac attaggagaa caaattttca gcattgaagg tactgttcaa ggaggagaca   1260
actttcagat ggaaatgtca caagtgggat tcagtgcaga ttactcttct caaaatgata   1320
ttctgatgct gggtgcagtg ggagcttttg gctggagtgg gaccattgtc cagaagacat   1380
ctcatggcca tttgatcttt cctaaacaag cctttgacca aattctgcag gacagaaatc   1440
acagttcata tttaggttac tctgtggctg caatttctac tggagaaagc actcactttg   1500
ttgctggtgc tcctcgggca aattataccg gccagatagt gctatatagt gtgaatgaga   1560
atggcaatat cacggttatt caggctcacc gaggtgacca gattggctcc tattttggta   1620
gtgtgctgtg ttcagttgat gtggataaag acaccattac agacgtgctc ttggtaggtg   1680
caccaatgta catgagtgac ctaaagaaag aggaaggaag agtctacctg tttactatca   1740
aagagggcat tttgggtcag caccaatttc ttgaaggccc cgagggcatt gaaaacactc   1800
gatttggttc agcaattgca gctctttcag acatcaacat ggatggcttt aatgatgtga   1860
ttgttggttc accactagaa aatcagaatt ctggagctgt atacatttac aatggtcatc   1920
agggcactat ccgcacaaag tattcccaga aaatcttggg atccgatgga gcctttagga   1980
gccatctcca gtactttggg aggtccttgg atggctatgg agatttaaat ggggattcca   2040
tcaccgatgt gtctattggt gcctttggac aagtggttca actctggtca caaagtattg   2100
ctgatgtagc tatagaagct tcattcacac cagaaaaaat cactttggtc aacaagaatg   2160
ctcagataat tctcaaactc tgcttcagtg caaagttcag acctactaag caaaacaatc   2220
aagtggccat tgtatataac atcacacttg atgcagatgg attttcatcc agagtaacct   2280
ccagggggtt atttaaagaa aacaatgaaa ggtgcctgca gaagaatatg gtagtaaatc   2340
aagcacagag ttgccccgag cacatcattt atatacagga gccctctgat gttgtcaact   2400
ctttggattt gcgtgtggac atcagtctgg aaaaccctgg cactagccct gcccttgaag   2460
cctattctga gactgccaag gtcttcagta ttcctttcca caaagactgt ggtgaggacg   2520
gactttgcat ttctgatcta gtcctagatg tccgacaaat accagctgct caagaacaac   2580
cctttattgt cagcaaccaa aacaaaaggt taacattttc agtaacgctg aaaaataaaa   2640
gggaaagtgc atacaacact ggaattgttg ttgatttttc agaaaacttg ttttttgcat   2700
cattctccct gccggttgat gggacagaag taacatgcca ggtggctgca tctcagaagt   2760
ctgttgcctg cgatgtaggc taccctgctt taaagagaga acaacaggtg acttttacta   2820
```

-continued

```
ttaactttga cttcaatctt caaaaccttc agaatcaggc gtctctcagt ttccaagcct   2880
taagtgaaag ccaagaagaa aacaaggctg ataatttggt caacctcaaa attcctctcc   2940
tgtatgatgc tgaaattcac ttaacaagat ctaccaacat aaatttttat gaaatctctt   3000
cggatgggaa tgttccttca atcgtgcaca gttttgaaga tgttggtcca aaattcatct   3060
tctccctgaa ggtaacaaca ggaagtgttc cagtaagcat ggcaactgta atcatccaca   3120
tccctcagta taccaaagaa aagaacccac tgatgtacct aactggggtg caaacagaca   3180
aggctggtga catcagttgt aatgcagata tcaatccact gaaaatagga caaacatctt   3240
cttctgtatc tttcaaaagt gaaaatttca ggcacaccaa agaattgaac tgcagaactg   3300
cttcctgtag taatgttacc tgctggttga aagacgttca catgaaagga gaatactttg   3360
ttaatgtgac taccagaatt tggaacggga ctttcgcatc atcaacgttc cagacagtac   3420
agctaacggc agctgcagaa atcaacacct ataaccctga gatatatgtg attgaagata   3480
acactgttac gattcccctg atgataatga aacctgatga gaaagccgaa gtaccaacag   3540
gagttataat aggaagtata attgctggaa tccttttgct gttagctctg gttgcaattt   3600
tatggaagct cggcttcttc aaaagaaaat atgaaaagat gaccaaaaat ccagatgaga   3660
ttgatgagac cacagagctc agtagctgaa ccagcagacc tacctgcagt gggaaccggc   3720
agcatcccag ccagggtttg ctgtttgcgt gaatggattt ctttttaaat cccatatttt   3780
ttttatcatg tcgtaggtaa actaacctgg tattttaaga gaaaactgca ggtcagtttg   3840
gaatgaagaa attgtggggg gtgggggagg tgcggggggc aggtagggaa ataataggga   3900
aaatacctat tttatatgat gggggaaaaa aagtaatctt taaactggct ggcccagagt   3960
ttacattcta atttgcattg tgtcagaaac atgaaatgct tccaagcatg acaactttta   4020
aagaaaaata tgatactctc agattttaag gggaaaaact gttctcttta aaatatttgt   4080
ctttaaacag caactacaga agtggaagtg cttgatatgt aagtacttcc acttgtgtat   4140
attttaatga atattgatgt taacaagagg ggaaaacaaa acacaggttt tttcaattta   4200
tgctgctcat ccaaagttgc cacagatgat acttccaagt gataatttta tttataaact   4260
aggtaaaatt tgttgttggt tccttttaga ccacggctgc cccttccaca ccccatcttg   4320
ctctaatgat caaaacatgc ttgaataact gagcttagag tatacctcct atatgtccat   4380
ttaagttagg agagggggcg atatagagaa taaggcacaa aattttgttt aaaactcaga   4440
atataacatg taaaatccca tctgctagaa gcccatcctg tgccagagga aggaaaagga   4500
ggaaatttcc tttctctttt aggaggcaca acagttctct tctaggattt gtttggctga   4560
ctggcagtaa cctagtgaat ttctgaaaga tgagtaattt ctttggcaac cttcctcctc   4620
ccttactgaa ccactctccc acctcctggt ggtaccatta ttatagaagc cctctacagc   4680
ctgactttct ctccagcggt ccaaagttat cccctccttt acccctcatc caaagttccc   4740
actccttcag gacagctgct gtgcattaga tattaggggg gaaagtcatc tgtttaattt   4800
acacacttgc atgaattact gtatataaac tccttaactt cagggagcta ttttcattta   4860
gtgctaaaca agtaagaaaa ataagctcga gtgaatttct aaatgttgga atgttatggg   4920
atgtaaacaa tgtaaagtaa gacatctcag gatttcacca gaagttacag atgaggcact   4980
ggaagccacc aaattagcag gtgcaccttc tgtggctgtc ttgtttctga agtacttaaa   5040
cttccacaag agtgaatttg acctaggcaa gtttgttcaa aaggtagatc ctgagatgat   5100
ttggtcagat tgggataagg cccagcaatc tgcattttaa caagcacccc agtcactagg   5160
atgcagatgg accacacttt gagaaacacc acccatttct actttttgca ccttattttc   5220
```

-continued

```
tctgttcctg agcccccaca ttctctagga gaaacttaga ggaaaagggc acagacacta   5280
catatctaaa gctttggaca agtccttgac ctctataaac ttcagagtcc tcattataaa   5340
atgggaagac tgagctggag ttcagcagtg atgcttttag ttttaaaagt ctatgatctg   5400
gacttcctat aatacaaata cacaatcctc caagaatttg acttggaaaa aaatgtcaaa   5460
ggaaaacagg ttatctgccc atgtgcatat ggacaacctt gactaccctg gcctggcccg   5520
tggtggcagt ccagggctat ctgtactgtt tacagaatta ctttgtagtt gacaacacaa   5580
aacaaacaaa aaaggcataa aatgccagcg gtttatagaa aaaacagcat ggtattctcc   5640
agttaggtat gccagagtcc aattctttta acagctgtga gaatttgctg cttcattcca   5700
acaaaatttt atttaaaaaa aaaaaaaaaa gactggagaa actagtcatt agcttgataa   5760
agaatattta acagctagtg gtgctggtgt gtacctgaag ctccagctac ttgagagact   5820
gagacaggaa gatcgcttga gcccaggagt tcaagtccag cctaagcaac atagcaagac   5880
cctgtctcaa aaaaatgact atttaaaaag acaatgtggc caggcacggt ggctcacacc   5940
tgtaatccca acactttggg aggctgaggc cggtggatca cgaggtcagg agtttgagac   6000
tagcctggcc aacatggtga aaccccatct ctaataatat aaaaattagc tgggcgtagt   6060
agcaggtgcc tgtaatccca gttactcggg aagctgaggc aggagaatca cttgaacccg   6120
ggaggcagag gtttcagtga gccgagatcg cgccactgca ctccagcctg ggtgacaggg   6180
caagactctg tctcaaacaa acaaacaaaa aaaaagttag tactgtatat gtaaatacta   6240
gcttttcaat gtgctataca aacaattata gcacatcctt ccttttactc tgtctcacct   6300
cctttaggtg agtacttcct taaataagtg ctaaacatac atatacggaa cttgaaagct   6360
ttggttagcc ttgccttagg taatcagcct agtttacact gtttccaggg agtagttgaa   6420
ttactataaa ccattagcca cttgtctctg caccatttat cacaccagga cagggtctct   6480
caacctgggc gctactgtca tttggggcca ggtgattctt ccttgcaggg gctgtcctgt   6540
accttgtagg acagcagccc tgtcctagaa ggtatgttta gcagcattcc tggcctctag   6600
ctacccgatg ccagagcatg ctccccccgc agtcatgaca atcaaaaaat gtctccagac   6660
attgtcaaat gcctcctggg gggcagtatt tctcaagcac ttttaagcaa aggtaagtat   6720
tcatacaaga aatttagggg gaaaaaacat tgtttaaata aaagctatgt gttcctattc   6780
aacaatattt ttgctttaaa agtaagtaga gggcataaaa gatgtcatat tcaaatttcc   6840
atttcataaa tggtgtacag acaaggtcta tagaatgtgg taaaaacttg actgcaacac   6900
aaggcttata aaatagtaag atagtaaaat agcttatgaa gaaactacag agatttaaaa   6960
ttgtgcatga ctcatttcag cagcaaaata agaactccta actgaacaga aatttttcta   7020
cctagcaatg ttattcttgt aaaatagtta cctattaaaa ctgtgaagag taaaactaaa   7080
gccaatttat tatagtcaca caagtgatta tactaaaaat tattataaag gttataattt   7140
tataatgtat ttacctgtcc tgatatatag ctataaccca atatatgaaa atctcaaaaa   7200
ttaagacatc atcatacaga aggcaggatt ccttaaactg agatccctga tccatcttta   7260
atatttcaat ttgcacacat aaaacaatgc ccttttgtgt acattcaggc atacccattt   7320
taatcaattt gaaaggttaa tttaaacctc tagaggtgaa tgagaaacat gggggaaaag   7380
tatgaaatag gtgaaaatct taactatttc tttgaactct aaagactgaa actgtagcca   7440
ttatgtaaat aaagtttcat atgtacctgt ttattttggc agattaagtc aaaatatgaa   7500
tgtatatatt gcataactat gttagaattg tatatatttt aaagaaattg tcttggatat   7560
```

-continued

```
tttcctttat acataataga taagtctttt ttcaaatgtg gtgtttgatg tttttgatta   7620

aatgtgtttt gcctctttcc acaaaaactg taaaaataaa tgcatgtttg tacaaaaagt   7680

tgcagaattc atttgattta tgagaaacaa aaattaaatt gtagtcaaca gttagtagtt   7740

tttctcatat ccaagtataa caaacagaaa agtttcatta ttgtaaccca ctttttttcat  7800

accacattat tgaatattgt tacaattgtt ttgaaaataa agccattttc tttgggcttt   7860

tataagttaa aaaaaaaa                                                7878
```

TUMOR MARKER, AND METHOD FOR COLLECTING AND DETECTING TUMOR CELL IN DISTINCTION FROM CONTAMINANT CELL

This application is a national phase entry under 35 U.S.C. § 371 of PCT Patent Application No. PCT/JP2019/007470, filed on Feb. 27, 2019, which claims priority under 35 U.S.C. § 119 to Japanese Patent Application No. 2018-042710, filed Mar. 9, 2018, Japanese Patent Application No. 2018-105966, filed Jun. 1, 2018, and Japan Patent Application No. 2018-193273, filed Oct. 12, 2018, all of which are incorporated by reference. Also, the Sequence Listing filed electronically herewith is hereby incorporated by reference (File name: 2020-09-08T_258-001_Seq_List; File size: 53 KB; Date recorded: Sep. 8, 2020).

TECHNICAL FIELD

The present invention relates to a tumor marker, and a method of collecting and detecting a tumor cell contained in a sample. In particular, the present invention relates to a method which uses a protein or gene expressed by a tumor cell contained in a sample, to collect and detect the tumor cell in distinct from a contaminant cell contained in the sample.

BACKGROUND ART

A tumor cell that has left a primary lesion infiltrates a blood vessel or lymph vessel, and then circulates in blood or lymph fluid, finally invading another organ or tissue to form a metastatic lesion. The tumor cell that circulates in blood is also called CTC (Circulating Tumor Cell), and a large number of clinical trials and studies have been carried out therefor. For example, the number of CTCs contained in blood collected from a patient is counted (Patent Document 1), or protein expression, or gene mutation or translocation, in the CTCs is investigated to provide information related to prediction of prognosis or cancer recurrence in the patient. However, since the number of CTCs contained in blood is very small, and various contaminant cells such as erythrocytes and leukocytes are contained in blood, CTC detection/analysis requires a technique which enables collection and detection of a very small number of cells in distinction from a large number of cells.

Conventionally, detection of CTCs has been carried out using a protein (tumor marker) expressed in CTCs such as cytokeratin or EpCAM (Epithelial Cell Adhesion Molecule) (Patent Document 1). However, cytokeratin has the problem of crossing with (non-specific detection of) contaminant cells contained in blood, and EpCAM has the problem that the collection and detection are possible only for part of epithelium-derived CTCs.

PRIOR ART DOCUMENT

Patent Document

[Patent Document 1] Japanese Translated PCT Patent Application Laid-open No. 2008-533487

SUMMARY OF THE INVENTION

Problems to be Solved by the Invention

An object of the present invention is to provide a tumor marker, and a method of collecting and detecting a tumor cell contained in a sample in distinction from a contaminant cell contained in the sample.

Means for Solving the Problems

In order to solve the problems described above, the present inventors carried out comparative expression analysis using a next-generation sequencer between 10 cancer cell lines and, as samples from healthy individuals, leukocytes, to discover tumor markers with which tumor cells contained in a sample can be collected and detected in distinction from contaminant cells contained in the sample, thereby reaching the present invention.

More specifically, the present invention can be exemplified as follows.

[1] A method of detecting a tumor cell contained in a sample in distinction from a contaminant cell, the method comprising detecting one or more polypeptides selected from the group consisting of the following (i) to (iii) present in the sample:

(i) a polypeptide comprising at least the amino acid sequence of any of SEQ ID NOs:1 to 6;

(ii) a polypeptide comprising an amino acid sequence having a homology of not less than 70% to the amino acid sequence of any of SEQ ID NOs:1 to 6; and (iii) a polypeptide comprising at least a splicing variant of the amino acid sequence of any of SEQ ID NOs:1 to 6, or a polypeptide comprising at least a splicing variant of a polypeptide having a homology of not less than 70% to the amino acid sequence of any of SEQ ID NOs:1 to 6.

[2] The method according to [1], wherein the detection is carried out using an antibody or aptamer that specifically recognizes one or more polypeptides selected from the group consisting of (i) to (iii).

[3] A method of detecting a tumor cell contained in a sample in distinction from a contaminant cell, the method comprising detecting a gene encoding any of the following polypeptides (i) to (iii) present in the sample:

(i) a polypeptide comprising at least the amino acid sequence of any of SEQ ID NOs:1 to 6;

(ii) a polypeptide comprising an amino acid sequence having a homology of not less than 70% to the amino acid sequence of any of SEQ ID NOs:1 to 6; and (iii) a polypeptide comprising at least a splicing variant of the amino acid sequence of any of SEQ ID NOs:1 to 6, or a polypeptide comprising at least a splicing variant of a polypeptide having a homology of not less than 70% to the amino acid sequence of any of SEQ ID NOs:1 to 6.

[4] A method of collecting a tumor cell, the method comprising: detecting a tumor cell contained in a sample in distinction from a contaminant cell; and collecting the detected tumor cell using collection means;

wherein the detection of the tumor cell is carried out by detecting one or more polypeptides selected from the group consisting of the following (i) to (iii) present in the sample:

(i) a polypeptide comprising at least the amino acid sequence of any of SEQ ID NOs:1 to 6;

(ii) a polypeptide comprising at least an amino acid sequence having a homology of not less than 70% to the amino acid sequence of any of SEQ ID NOs:1 to 6; and (iii) a polypeptide comprising at least a splicing variant of the amino acid sequence of any of SEQ ID NOs:1 to 6, or a polypeptide comprising at least a splicing variant of a polypeptide having a homology of not less than 70% to the amino acid sequence of any of SEQ ID NOs:1 to 6.

[5] The method according to [4], wherein the detection of the tumor cell is carried out using an antibody or aptamer that specifically recognizes one or more polypeptides selected from the group consisting of (i) to (iii).

[6] The method according to any of [1] to [5], wherein the sample is blood, and the contaminant cell contained in the sample is leukocyte.

[7] A tumor marker comprising any of the following polypeptides (i) to (iii):

(i) a polypeptide comprising at least the amino acid sequence of any of SEQ ID NOs:1 to 6;

(ii) a polypeptide comprising at least an amino acid sequence having a homology of not less than 70% to the amino acid sequence of any of SEQ ID NOs:1 to 6; and (iii) a polypeptide comprising at least a splicing variant of the amino acid sequence of any of SEQ ID NOs:1 to 6, or a polypeptide comprising at least a splicing variant of a polypeptide having a homology of not less than 70% to the amino acid sequence of any of SEQ ID NOs:1 to 6;

the tumor marker being capable of detecting a tumor cell contained in a sample in distinction from leukocyte contained in the sample.

[8] A tumor marker comprising a gene encoding any of the following polypeptides (i) to (iii):

(i) a polypeptide comprising at least the amino acid sequence of any of SEQ ID NOs:1 to 6;

(ii) a polypeptide comprising at least an amino acid sequence having a homology of not less than 70% to the amino acid sequence of any of SEQ ID NOs:1 to 6; and (iii) a polypeptide comprising at least a splicing variant of the amino acid sequence of any of SEQ ID NOs:1 to 6, or a polypeptide comprising at least a splicing variant of a polypeptide having a homology of not less than 70% to the amino acid sequence of any of SEQ ID NOs:1 to 6;

the tumor marker being capable of detecting a tumor cell contained in a sample in distinction from leukocyte contained in the sample.

[9] A tumor marker comprising any of the following polypeptides (i) to (iii):

(i) a polypeptide comprising at least the amino acid sequence of any of SEQ ID NOs:1 to 6;

(ii) a polypeptide comprising at least an amino acid sequence having a homology of not less than 70% to the amino acid sequence of any of SEQ ID NOs:1 to 6; and (iii) a polypeptide comprising at least a splicing variant of the amino acid sequence of any of SEQ ID NOs:1 to 6, or a polypeptide comprising at least a splicing variant of a polypeptide having a homology of not less than 70% to the amino acid sequence of any of SEQ ID NOs:1 to 6;

which tumor marker enables collection of a tumor cell contained in a sample in distinction from leukocyte contained in the sample.

The present invention is described below in detail.

Examples of the sample in the present invention include not only a tissue, whole blood, ascites, or the like collected from a patient, but also samples prepared by diluting the tissue, whole blood, ascites, or the like using an appropriate buffer; components derived from whole blood, such as serum, plasma, cord blood, or blood component fluid; and suspensions prepared by suspending, in an appropriate buffer, a piece of a tissue containing blood such as a liver, lung, spleen, kidney, tumor, or lymph node tissue. Examples of the sample in the present invention also include fractions containing a tumor cell, which fractions are obtained by separation/collection from these samples and suspensions by centrifugation or the like.

The contaminant cell contained in the sample in the present invention means cell(s) other than tumor cells, and examples of the contaminant cell include erythrocytes, leukocytes, and platelets in cases where the sample is a blood sample such as whole blood, a whole blood dilution, a component derived from whole blood, a suspension of a tissue containing blood, or a fraction containing a tumor cell obtained from these samples or suspensions. In particular, the method of detecting a tumor cell of the present invention is an excellent method for distinguishing a tumor cell from leukocyte contained in a blood sample, which often led to false-positives in the conventional methods of detecting a tumor cell. Further, the method of collecting a tumor cell of the present invention is an excellent method for collecting an EpCAM (Epithelial Cell Adhesion Molecule)-negative tumor cell contained in a blood sample, which often led to false-negatives in the conventional methods of collecting a tumor cell.

In the detection of a tumor cell in the present invention, the tumor cell contained in the sample may be directly detected by staining, a probe hybridization method, or the like based on any of the polypeptides (i) to (iii) or the gene encoding the polypeptide which is present in the cell and derived from the cell, or the tumor cell may be indirectly detected by detecting any of the polypeptides (i) to (iii) or the gene encoding the polypeptide which is secreted and derived from the tumor cell contained in the sample.

In the present invention, the tumor cell is detected based on the expression level of any of the polypeptides (i) to (iii) or the gene encoding the polypeptide derived from the tumor cell. The detection may be carried out qualitatively, that is, based on the presence or absence of the tumor cell, or may be carried out quantitatively, that is, based on the number of tumor cells or detected intensity. The criterion for the detection is also not limited. For example, a cell may be judged as a tumor cell even when a very low detection signal is found. Alternatively, a cell may be judged as a tumor cell when the detection signal is not weaker than a certain threshold. Alternatively, a cell may be judged as a tumor cell when the signal is not weaker than a certain value relative to a signal from a contaminant cell contained in the sample (erythrocytes, leukocytes, and/or the like in cases of a blood sample), or when the signal is not less than 2SD, not less than 3SD, or not less than 4SD from the average of the signal from such contaminant cells.

The collection of the tumor cell in the present invention may be carried out by detecting any of the polypeptides (i) to (iii) which is present in the cell and derived from the cell, to detect the tumor cell contained in the sample in distinction from the contaminant cell, and then collecting the detected tumor cell using collection means. The "any of the polypeptides (i) to (iii)" is a transmembrane polypeptide in all cases.

In the present invention, the detection and/or collection of the tumor cell contained in the sample is/are carried out using any of the polypeptides (i) to (iii), which is a protein expressed by the tumor cell.

The polypeptide consisting of the amino acid sequence of SEQ ID NO:1 is a protein called TM4SF1 (Transmembrane 4 L six family member 1), L6, M3S1, TAAL6, or H-L6. Its amino acid sequence is presented in GenBank No. NP_055035.1.

The polypeptide consisting of the amino acid sequence of SEQ ID NO:2 is a protein called TNFRSF12A (TNF receptor superfamily member 12A), FN14, TWEAKR, or CD266. Its amino acid sequence is presented in GenBank No. NP_057723.1.

The polypeptide consisting of the amino acid sequence of SEQ ID NO:3 is a protein called SDC1 (Syndecan 1), SDC, SYND1, syndecan, or CD138. Its amino acid sequence is presented in GenBank No. NP_002988.3.

The polypeptide consisting of the amino acid sequence of SEQ ID NO:4 is a protein called F3 (Coagulation factor III, tissue factor), TF, TFA, or CD142. Its amino acid sequence is presented in GenBank No. NP_001984.1.

The polypeptide consisting of the amino acid sequence of SEQ ID NO:5 is a protein called EPHA2 (EPH receptor A2), CTPA, CTPP1, CTRCT6, ECK, or ARCC2. Its amino acid sequence is presented in GenBank No. NP_004422.2.

The polypeptide consisting of the amino acid sequence of SEQ ID NO:6 is a protein called ITGA2 (Integrin subunit alpha 2), CD49B, GPIa, HPA-5, VLA-2, VLAA2, or BR. Its amino acid sequence is presented in GenBank No. NP_002194.2.

In particular, as shown below in Examples, TM4SF1 (SEQ ID NO:1) and TNFRSF12A (SEQ ID NO:2) are highly expressed, irrespective of the cancer type, in lung adenocarcinoma cells, breast adenocarcinoma cells, breast cancer cells, prostate cancer cells, liver cancer cells, and pancreatic cancer cells. Thus, a wider range of tumor cells contained in a sample can be detected therewith than with EpCAM, which is a tumor marker used in conventional detection. Since TM4SF1 (SEQ ID NO:1) and TNFRSF12A (SEQ ID NO:2) are transmembrane proteins, a wider range of tumor cells contained in a sample can be collected therewith than with EpCAM, which is a tumor marker used in conventional collection.

In cases where a pancreatic cancer cell is to be specifically detected, it is suggested, based on the result of gene expression analysis shown below in Examples, that ITGA2 (SEQ ID NO:6) is preferably used. Since ITGA2 (SEQ ID NO:6) is a transmembrane protein, it is suggested that the protein is preferably used in cases where pancreatic cancer cell is to be specifically collected.

The present invention includes a mode in which one or several amino acid residues in any of the amino acid sequences of SEQ ID NOs: 1 to 6 are substituted with other amino acid residues or deleted, or in which one or several amino acid residues are inserted into any of the amino acid sequences of SEQ ID NOs: 1 to 6, as long as the same activity as that of the protein consisting of the amino acid sequence of any of SEQ ID NOs:1 to 6 is maintained. In the present description, the term "several" means an integer of 20, 19, 18, 17, 16, 15, 14, 13, 12, 11, 10, 9, 8, 7, 6, 5, 4, 3, or 2. The term "one or several amino acid residues" preferably means 1 to 10 amino acid residues, more preferably 1 to 5 amino acid residues, still more preferably 1 to 3 amino acid residues, especially preferably 2 or less amino acid residues.

Similarly, each polypeptide may be in a mode in which one or more amino acid residues are added to the N-terminus and/or C-terminus of the polypeptide, as long as the function as the protein is maintained. The marker used in the method of the present invention may be a protein having a homology of not less than 70% to the entire amino acid sequence of any of SEQ ID NOs:1 to 6, as long as the marker has the same activity as that of the protein consisting of the amino acid sequence of any of SEQ ID NOs:1 to 6. The protein has a homology of preferably not less than 80%, more preferably not less than 90%, still more preferably not less than 95%.

When a protein is expressed from the gene encoding the protein in a eukaryotic cell, a reaction (splicing) occurs to remove an intron(s) from a gene (RNA) precursor and to bind the exons before and after the intron(s) to each other. Since the exons remained have diversity, and produce various mature mRNAs, proteins having different activities (splicing variants) are expressed in some cases. The polypeptides that may be used for the detection in the present invention also include:

a polypeptide comprising at least a splicing variant of the amino acid sequence of any of SEQ ID NOs:1 to 6;

a polypeptide comprising at least a splicing variant of an amino acid sequence which is the same as the amino acid sequence of any of SEQ ID NOs:1 to 6 except that one or several amino acid residues are substituted with other amino acid residues or deleted;

a polypeptide comprising at least a splicing variant of an amino acid sequence which is the same as the amino acid sequence of any of SEQ ID NOs:1 to 6 except that one or several amino acid residues are inserted; and a polypeptide comprising at least a splicing variant of a polypeptide having a homology of not less than 70% to the amino acid sequence of any of SEQ ID NOs:1 to 6.

When the detection of the present invention is carried out, a dye (such as a chemiluminescent dye or fluorescent dye) which enables specific labeling of any of the polypeptides described above in (i) to (iii) may be added to perform staining, and then the detection may be carried out based on the stained image or staining intensity (such as the luminescence intensity or fluorescence intensity). However, from the viewpoint of versatility, the detection is generally carried out by a method using an antibody (hereinafter also simply referred to as anti-polypeptide antibody) or aptamer against the above-described polypeptide. Such a method can be said to be a preferred mode also from the viewpoint of applicability to both the direct detection and the indirect detection.

Since the polypeptides described in (i) to (iii) are transmembrane proteins, they can also be tumor markers with which a tumor cell contained in a sample can be collected in distinction from leukocyte contained in the sample.

Preferably, when the tumor cell contained in the sample is detected using an anti-polypeptide antibody, the antibody is modified with a labeling substance by a certain method, and the detection is carried out based on the presence or absence, or the amount, of the labeling substance. The labeling substance may be appropriately selected from substances normally used in the field of measurement using antigen-antibody reaction. Examples of the labeling substance include fluorescent substances such as fluorescein; enzymes such as alkaline phosphatase; and radioactive substances. The binding mode between the antibody and the labeling substance is not limited. The mode may be a mode in which the antibody is directly bound to the labeling substance by chemical bonding or the like, or may be a mode in which the antibody is indirectly bound through an antibody against the antibody, to which the labeling substance is bound (labeled secondary antibody). The detection format for the tumor cell contained in the sample using the anti-polypeptide antibody is not limited. The cell may be manually detected by the ELISA (Enzyme-Linked ImmunoSorbent Assay) method or the Western blotting method, or may be automatically detected using an enzyme immunoassay apparatus such as AIA-900 or AIA-CL2400 (these are manufactured by Tosoh Corporation).

Thus, the polypeptides described in (i) to (iii) can be tumor markers with which a tumor cell contained in a sample can be detected in distinction from leukocyte contained in the sample.

The collection of the tumor cell in distinction from the contaminant cell by the present invention may be carried out by using the polypeptide of any of (i) to (iii) to detect the tumor cell in distinction from the contaminant cell, and then collecting the detected tumor cell using collection means. Examples of the collection means include means comprising: a substrate provided with a retaining section capable of retaining the tumor cell; and a collecting section for collecting the tumor cell by suction and discharge by a nozzle. Specific examples of the collection means include the collection apparatus disclosed in JP 2016-142616 A.

On the other hand, in the present invention, the gene encoding any of the polypeptides (i) to (iii) is not limited as long as it is a polynucleotide obtained by converting any of the polypeptides (i) to (iii) using codons. The gene is preferably a polynucleotide obtained by conversion using human-type codons.

Examples of the gene encoding a polypeptide comprising at least a polypeptide consisting of the amino acid sequence of any of SEQ ID NOs:1 to 6 include the following sequences:

a polynucleotide consisting of nucleotide positions 235 to 840 of the sequence of SEQ ID NO:7 (GenBank No. NM_014220.2), which is obtained by conversion of a polypeptide consisting of the sequence of SEQ ID NO:1;

a polynucleotide consisting of nucleotide positions 87 to 473 of the sequence of SEQ ID NO:8 (GenBank No. NM_016639.2), which is obtained by conversion of a polypeptide consisting of the sequence of SEQ ID NO:2;

a polynucleotide consisting of nucleotide positions 392 to 1321 of the sequence of SEQ ID NO:9 (GenBank No. NM_001006946.1), which is obtained by conversion of a polypeptide consisting of the sequence of SEQ ID NO:3;

a polynucleotide consisting of nucleotide positions 222 to 1106 of the sequence of SEQ ID NO:10 (GenBank No. NM_001993.4), which is obtained by conversion of a polypeptide consisting of the sequence of SEQ ID NO:4;

a polynucleotide consisting of nucleotide positions 156 to 3083 of the sequence of SEQ ID NO:11 (GenBank No. NM_004431.3), which is obtained by conversion of a polypeptide consisting of the sequence of SEQ ID NO:5; and a polynucleotide consisting of nucleotide positions 144 to 3686 of the sequence of SEQ ID NO:12 (GenBank No. NM_002203.3), which is obtained by conversion of a polypeptide consisting of the sequence of SEQ ID NO:6.

The method of detecting the gene described above is not limited. For example, a probe may be designed at an appropriate position in the polynucleotide, and then hybridization may be performed to detect the gene. Alternatively, a primer set may be designed at appropriate positions in the polynucleotide, and then the polynucleotide may be amplified and detected using the PCR method, RT-PCR method, TRC (Transcription Reverse transcription Concerted) method, NASBA (Nucleic Acid Sequence-Based Amplification) method, TMA (Transcription-Mediated Amplification) method, or the like. Alternatively, a sample containing the polynucleotide may be directly subjected to a sequencer to detect the gene.

Thus, the genes encoding the polypeptides described in (i) to (iii) can be tumor markers with which a tumor cell contained in a sample can be detected in distinction from leukocyte contained in the sample.

Effect of the Invention

According to the present invention, detection of tumor cell(s) contained in a sample can be carried out by detecting the polypeptide described in any of the following, or a gene encoding the polypeptide: (i) a polypeptide containing at least any of six amino acid sequences including TM4SF1 (GenBank No. NP_055035.1) and TNFRSF12A (GenBank No. NP_057723.1); (ii) a polypeptide containing an amino acid sequence having a homology of not less than 70% to the amino acid sequence of (i); and (iii) a polypeptide containing at least a splicing variant of the amino acid sequence of (i) or (ii). By the detection method, tumor cell(s) contained only in a small amount in a sample can be detected in distinction from contaminant cell(s) contained in the sample.

Further, collection of tumor cell(s) contained in a sample can be carried out by detecting the tumor cell(s) using the polypeptide described in any of (i) to (iii), and collecting the detected tumor cell(s) using collection means. By the collection method, tumor cell(s) contained only in a small amount in a sample can be collected in distinction from contaminant cell(s) contained in the sample.

BRIEF DESCRIPTION OF THE DRAWINGS

FIG. 1 is a diagram illustrating the result of TM4SF1 gene expression analysis of leukocytes of healthy individuals and various kinds of cancer cells.

FIG. 2 is a diagram illustrating the result of TNFRSF12A gene expression analysis of leukocytes of healthy individuals and various kinds of cancer cells.

FIG. 3 (*a*) and (*b*) are diagrams illustrating the result of immunostaining of a blood sample spiked with lung adenocarcinoma cells (PC14), which immunostaining was carried out using (a) an anti-TM4SF1 antibody and (b) an anti-CD45 antibody.

FIG. 4 (*a*) and (*b*) are diagrams illustrating the result of immunostaining of a blood sample spiked with pancreatic cancer cells (PANC1), which immunostaining was carried out using (a) an anti-TM4SF1 antibody and (b) an anti-CD45 antibody.

FIG. 5 (*a*) and (*b*) are diagrams illustrating the result of immunostaining of a blood sample spiked with lung adenocarcinoma cells (PC9), which immunostaining was carried out using (a) an anti-TNFRSF12A (CD266) antibody and (b) an anti-CD45 antibody.

FIG. 6 (*a*) and (*b*) are diagrams illustrating the result of immunostaining of a blood sample spiked with breast adenocarcinoma cells (MDAMB231), which immunostaining was carried out using (a) an anti-TNFRSF12A (CD266) antibody and (b) an anti-CD45 antibody.

FIG. 7 (*a*) and (*b*) are diagrams illustrating the result of immunostaining of a blood sample spiked with lung adenocarcinoma cells (PC9), which immunostaining was carried out using (a) an anti-CD142 (F3) antibody and (b) an anti-CD45 antibody.

FIG. 8 (*a*) and (*b*) are diagrams illustrating the result of immunostaining of a blood sample spiked with breast adenocarcinoma cells (MDAMB231), which immunostaining was carried out using (a) an anti-CD142 (F3) antibody and (b) an anti-CD45 antibody.

FIG. 9 (*a*) and (*b*) are diagrams illustrating the result of immunostaining of a blood sample spiked with prostate cancer cells (PC3), which immunostaining was carried out using (a) an anti-EPHA2 antibody and (b) an anti-CD45 antibody.

FIG. 10 (*a*) and (*b*) are diagrams illustrating the result of immunostaining of a blood sample spiked with pancreatic cancer cells (PANC1), which immunostaining was carried out using (a) an anti-ITGA2 antibody and (b) an anti-CD45 antibody.

FIG. 11 (*a*) and (*b*) are diagrams illustrating the result of immunostaining of a blood sample spiked with pancreatic cancer cells (AsPC-1), which immunostaining was carried out using (a) an anti-ITGA2 antibody and (b) an anti-CD45 antibody.

FIG. 12 (*a*) and (*b*) are diagrams illustrating the result of immunostaining of a blood sample spiked with breast cancer cells (SKBR3), which immunostaining was carried out using (a) an anti-SDC1 antibody and (b) an anti-CD45 antibody.

FIG. 13 (*a*) and (*b*) are diagrams illustrating the result of immunostaining of a blood sample spiked with pancreatic cancer cells (AsPC-1), which immunostaining was carried out using (a) an anti-SDC1 antibody and (b) an anti-CD45 antibody.

EXAMPLES

The present invention is described below in more detail by way of Examples for cases using a blood sample. However, the present invention is not limited to these Examples.

Example 1

Gene Expression Analysis of Leukocytes of Healthy Individuals and Various Kinds of Cancer Cells As cancer cell lines, the following 10 lines were selected: human lung adenocarcinoma cells (PC9 and PC14), human breast adenocarcinoma cells (MDAMB231), human breast cancer cells (SKBR3), human prostate cancer cells (22Rv1 and PC3), human liver cancer cells (HepG2 and HuH-7), and human pancreatic cancer cells (PANC1 and AsPC-1). Differences in the gene expression level between these cancer cell lines and leukocytes of healthy individuals were analyzed by the following method using a next-generation sequencer.

(1) The respective cancer cell lines were cultured using the following media in an environment at 5% $CO_2$ and 37° C. Thereafter, the cells were detached from the media using 0.25% trypsin/1 mM EDTA, to collect cancer cells as single cells (n=4). From RNA of each single cell, cDNA synthesis and amplification were carried out using a SMART-Seq v4 Ultra Low Input RNA Kit for Sequencing (Clontech). Similarly, leukocytes collected from blood of three healthy individuals were subjected to cDNA synthesis and amplification from RNA of each single cell (n=4).

PC9, PC14, and PANC1: DMEM (Dulbecco's Modified Eagle Medium)/Ham's F-12 medium supplemented with 10% (v/v) FBS (fetal bovine serum)

AsPC-1: RPMI-1640 medium supplemented with 10% (v/v) FBS and 1 mM pyruvic acid

MDAMB231: Leibovitz's L-15 medium with L-Glutamine, supplemented with 10% (v/v) FBS SKBR3: McCoy's 5a medium supplemented with 10% (v/v) FBS HepG2 and HuH-7: DMEM/high glucose medium supplemented with 10% (v/v) FBS 22Rv1: RPMI0211-1640 medium supplemented with 10% (v/v) FBS PC3: Ham's F-12K medium supplemented with 10% (v/v) FBS, and kanamycin and streptomycin (2) A plurality of cells obtained in (1) were collected, and total RNA was recovered therefrom using an RNeasy Mini Kit (QIAGEN). Thereafter, cDNA synthesis and amplification were carried out from 10 ng of the RNA using a SMART-Seq v4 Ultra Low Input RNA Kit for Sequencing (Clontech). Similarly, RNA was recovered from a plurality of leukocytes collected from blood of three healthy individuals, and cDNA synthesis and amplification were carried out from 10 ng of the RNA.

(3) Using 1 ng of the cDNA obtained in (1) and (2), library preparation was carried out using a Nextera XT DNA Library Preparation Kit (Illumina) and Nextera XT v2 Index Kit Set A (Illumina). By performing sequencing analysis using Next-seq500 (illumina) under single-end read conditions with a read length of 75 bp, not less than 10,000,000 sequence reads were read for each sample.

(4) The nucleotide sequences (sequence data) read in (3) were mapped on the human genome sequence using TopHat 2 (Johns Hopkins University) and Bowtie 2 (Johns Hopkins University). The human genome sequence and human gene information were obtained using BUILD GRCh38 published by NCBI (National Center for Biological Information). From the mapped nucleotide sequences, the expression value for each gene was determined in terms of the FPKM (Fragments Per Kilobase of exon per Million reads mapped) unit based on the number of reads of the gene obtained.

(5) Comparison of expression was carried out for 15 samples from 3 specimens of leukocytes of healthy individuals, and 48 samples from 10 kinds of cancer cell lines.

Table 1 shows the genes whose average expression values (FPKM values) in the cancer cell lines (10 kinds, 48 samples) were not less than 10.00 times higher than the average expression value (FPKM value) in the leukocytes of the healthy individuals (3 specimens, 15 samples), and which encode transmembrane proteins. FIG. 1 and FIG. 2 show the results of analysis of each sample regarding the genes encoding TM4SF1 (SEQ ID NO:1) and TNFRSF12A (SEQ ID NO:2), respectively, among the above genes. In the figures, PC9 or PC14 represents a result for human lung adenocarcinoma cells; MDAMB231 represents a result for human breast adenocarcinoma cells; SKBR3 represents a result for human breast cancer cells; HepG2 or HuH-7 represents a result for human liver cancer cells; AsPC-1 or PANC1 represents a result for human pancreatic cancer cells; 22Rv1 or PC3 represents a result for human prostate cancer cells; Leuco1 to Leuco3 represent results for leukocytes of healthy individuals; "single" represents a result for RNA in a single cell (n=4); and "10 ng" represents a result for RNA (10 ng) in a plurality of cells.

TABLE 1

| Name | Protein GenBank No. | SEQ ID NO | Gene GenBank No. | SEQ ID NO | gene expression values(FPKM + 1) cancer cells | leukocytes | cancer cells/ leukocytes |
|---|---|---|---|---|---|---|---|
| TM4SF1 | NP_055035.1 | 1 | NM_014220.2 | 7 | 342.22 | 1.04 | 329.87 |
| TNFRSF12A | NP_057723.1 | 2 | NM_016639.2 | 8 | 94.92 | 1.12 | 84.88 |
| SDC1 | NP_002988.3 | 3 | NM_001006946.1 | 9 | 18.28 | 1.01 | 18.15 |
| F3 | NP_001984.1 | 4 | NM_001993.4 | 10 | 14.72 | 1.03 | 14.36 |

It can be seen that the average expression value (FPKM value) of the TM4SF1 gene (SEQ ID NO:7) in the cancer cell lines (10 kinds, 48 samples) is not less than 300 times higher than the average FPKM value in the leukocytes (3 specimens, 15 samples), indicating that the TM4SF1 gene is specifically and highly expressed in the cancer cells (tumor cells) (Table 1). Further, since the TM4SF1 gene is highly expressed, irrespective of the cancer type, in lung adenocarcinoma cells, breast adenocarcinoma cells, breast cancer cells, liver cancer cells, pancreatic cancer cells, and prostate cancer cells (FIG. 1), it can be seen that a wider range of tumor cells contained in a sample can be detected with TM4SF1 protein (SEQ ID NO:1) or gene (SEQ ID NO:7) than with EpCAM, which is a tumor marker used in conventional detection. Since TM4SF1 protein (SEQ ID NO:1) is a transmembrane protein, it can be seen that a wider range of tumor cells contained in a sample can be collected therewith than with EpCAM, which is a tumor marker used in conventional collection.

Similarly, it can be seen that the average expression value (FPKM value) of the TNFRSF12A gene (SEQ ID NO:8) in the cancer cell lines (10 kinds, 48 samples) is not less than 50 times higher than the average FPKM value in the leukocytes (3 specimens, 15 samples), indicating that the TNFRSF12A gene is specifically and highly expressed in the cancer cells (tumor cells) (Table 1). Further, since the TNFRSF12A gene is highly expressed, irrespective of the cancer type, in lung adenocarcinoma cells, breast adenocarcinoma cells, breast cancer cells, liver cancer cells, pancreatic cancer cells, and prostate cancer cells (FIG. 2), it can be seen that a wider range of tumor cells contained in a sample can be detected with TNFRSF12A protein (SEQ ID NO:2) or gene (SEQ ID NO:8) than with EpCAM, which is a tumor marker used in conventional detection. Since TNFRSF12A protein (SEQ ID NO:2) is a transmembrane protein, it can be seen that a wider range of tumor cells contained in a sample can be collected therewith than with EpCAM, which is a tumor marker used in conventional collection.

Table 2 shows the genes whose average expression values (FPKM values) in the lung adenocarcinoma cell lines (2 kinds, 10 samples) were not less than 10.00 times higher than the average expression values (FPKM values) in the leukocytes of the healthy individuals (3 specimens, 15 samples), and which encode transmembrane proteins.

TABLE 2

| Name | Protein GenBank No. | SEQ ID NO | Gene GenBank No. | SEQ ID NO | gene expression values(FPKM + 1) lung adenocarcinoma cells | leukocytes | lung adenocarcinoma cells/ leukocytes |
|---|---|---|---|---|---|---|---|
| TM4SF1 | NP_055035.1 | 1 | NM_014220.2 | 7 | 523.66 | 1.04 | 504.76 |
| F3 | NP_001984.1 | 4 | NM_001993.4 | 10 | 154.43 | 1.03 | 150.65 |
| TNFRSF12A | NP_057723.1 | 2 | NM_016639.2 | 8 | 135.27 | 1.12 | 120.96 |
| SDC1 | NP_002988.3 | 3 | NM_001006946.1 | 9 | 12.92 | 1.01 | 12.83 |

Table 3 shows the genes whose average expression values (FPKM values) in the breast adenocarcinoma or breast cancer cell lines (2 kinds, 10 samples) were not less than 10.00 times higher than the average expression values (FPKM values) in the leukocytes of the healthy individuals (3 specimens, 15 samples), and which encode transmembrane proteins.

TABLE 3

| Name | Protein GenBank No. | SEQ ID NO | Gene GenBank No. | SEQ ID NO | gene expression values(FPKM + 1) breast adenocarcinoma or breast cancer cells | leukocytes | (breast adenocarcinoma or breast cancer cells)/ leukocytes |
|---|---|---|---|---|---|---|---|
| TNFRSF12A | NP_057723.1 | 2 | NM_016639.2 | 8 | 163.64 | 1.12 | 146.34 |
| TM4SF1 | NP_055035.1 | 1 | NM_014220.2 | 7 | 148.41 | 1.04 | 143.06 |
| F3 | NP_001984.1 | 4 | NM_001993.4 | 10 | 64.01 | 1.03 | 62.45 |
| SDC1 | NP_002988.3 | 3 | NM_001006946.1 | 9 | 26.59 | 1.01 | 26.41 |

Table 4 shows the genes whose average expression values (FPKM values) in the prostate cancer cell lines (2 kinds, 8 samples) were not less than 10.00 times higher than the average expression values (FPKM values) in the leukocytes of the healthy individuals (3 specimens, 15 samples), and which encode transmembrane proteins.

TABLE 4

| Name | Protein GenBank No. | Protein SEQ ID NO | Gene GenBank No. | Gene SEQ ID NO | gene expression values(FPKM + 1) prostate cancer cells | leukocytes | prostate cancer cells/ leukocytes |
|---|---|---|---|---|---|---|---|
| TM4SF1 | NP_055035.1 | 1 | NM_014220.2 | 7 | 67.80 | 1.04 | 65.36 |
| TNFRSF12A | NP_057723.1 | 2 | NM_016639.2 | 8 | 41.18 | 1.12 | 36.82 |
| SDC1 | NP_002988.3 | 3 | NM_001006946.1 | 9 | 22.00 | 1.01 | 21.85 |
| EPHA2 | NP_004422.2 | 5 | NM_004431.3 | 11 | 12.58 | 1.01 | 12.40 |

Table 5 shows the genes whose average expression values (FPKM values) in the liver cancer cell lines (2 kinds, 10 samples) were not less than 10.00 times higher than the average expression values (FPKM values) in the leukocytes of the healthy individuals (3 specimens, 15 samples), and which encode transmembrane proteins.

TABLE 5

| Name | Protein GenBank No. | Protein SEQ ID NO | Gene GenBank No. | Gene SEQ ID NO | gene expression values(FPKM + 1) liver cancer cells | leukocytes | liver cancer cells/ leukocytes |
|---|---|---|---|---|---|---|---|
| TM4SF1 | NP_055035.1 | 1 | NM_014220.2 | 7 | 743.44 | 1.04 | 716.61 |
| TNFRSF12A | NP_057723.1 | 2 | NM_016639.2 | 8 | 41.97 | 1.12 | 37.53 |

Table 6 shows the genes whose average expression values (FPKM values) in the pancreatic cancer cell lines (2 kinds, 10 samples) were not less than 10.00 times higher than the average expression values (FPKM values) in the leukocytes of the healthy individuals (3 specimens, 15 samples), and which encode transmembrane proteins.

TABLE 6

| Name | Protein GenBank No. | Protein SEQ ID NO | Gene GenBank No. | Gene SEQ ID NO | gene expression values(FPKM + 1) pancreatic cancer cells | leukocytes | pancreatic cancer cells/ leukocytes |
|---|---|---|---|---|---|---|---|
| TM4SF1 | NP_055035.1 | 1 | NM_014220.2 | 7 | 866.75 | 1.04 | 835.47 |
| TNFRSF12A | NP_057723.1 | 2 | NM_016639.2 | 8 | 170.47 | 1.12 | 152.45 |
| SDC1 | NP_002988.3 | 3 | NM_001006946.1 | 9 | 35.38 | 1.01 | 35.13 |
| EPHA2 | NP_004422.2 | 5 | NM_004431.3 | 11 | 15.01 | 1.01 | 14.79 |
| ITGA2 | NP_002194.2 | 6 | NM_002203.3 | 12 | 14.20 | 1.03 | 13.75 |

Among the genes shown in Table 1, whose average expression values (FPKM values) in the cancer cell lines (10 kinds, 48 samples) were not less than 10.00 times higher than the average expression values (FPKM values) in the leukocytes of the healthy individuals (3 specimens, 15 samples), the genes whose average expression values (FPKM values) were not less than 10.00 times higher in the cells of all cancer types (lung adenocarcinoma, breast adenocarcinoma or breast cancer, prostate cancer, liver cancer, and pancreatic cancer) than in the leukocytes of the healthy individuals (3 specimens, 15 samples) are shown in Table 7. As described above, it is suggested that a wider range of tumor cells contained in a sample can be detected with the proteins and genes shown in this table than with EpCAM, which is a tumor marker used in conventional detection. Further, since the proteins shown in this table are transmembrane proteins, it is suggested, as described above, that a wider range of tumor cells contained in a sample can be collected therewith than with EpCAM, which is a tumor marker used in conventional collection.

TABLE 7

| | SEQ ID NO | | upper: gene expression values(FPKM + 1), lower: gene expression ratio to leukocytes | | | | | |
|---|---|---|---|---|---|---|---|---|
| Name | Protein | Gene | leukocytes | lung adenocarcinoma cells | breast adenocarcinoma or breast cancer cells | prostate cancer cells | liver cancer cells | pancreatic cancer cells |
| TM4SF1 | 1 | 7 | 1.04 | 523.66 | 148.41 | 67.80 | 743.44 | 866.75 |
| | | | — | 504.76 | 143.06 | 65.36 | 716.61 | 835.47 |
| TNFRSF12A | 2 | 8 | 1.12 | 135.27 | 163.64 | 41.18 | 41.97 | 170.47 |
| | | | — | 120.96 | 146.34 | 36.82 | 37.53 | 152.45 |

Among the genes shown in Table 6, whose average expression values (FPKM values) in the pancreatic cancer cell lines (2 kinds, 10 samples) were not less than 10.00 times higher than the average expression values (FPKM values) in the leukocytes of the healthy individuals (3 specimens, 15 samples), the gene whose average expression values (FPKM values) in all cell lines other than pancreatic cancer (lung adenocarcinoma, breast adenocarcinoma or breast cancer, prostate cancer, and liver cancer) were less than 10.00 times the average expression value (FPKM values) in the leukocytes of the healthy individuals (3 specimens, 15 samples) is shown in Table 8. It is suggested that pancreatic cancer cells can be specifically detected with the protein and gene shown in this table. Further, since the protein shown in Table is a transmembrane protein, it is suggested that pancreatic cancer cells can be specifically collected therewith.

TABLE 8

| | SEQ ID NO | | upper: gene expression values(FPKM + 1), lower: gene expression ratio to leukocytes | | | | | |
|---|---|---|---|---|---|---|---|---|
| Name | Protein | Gene | leukocytes | lung adenocarcinoma cells | breast adenocarcinoma or breast cancer cells | prostate cancer cells | liver cancer cells | pancreatic cancer cells |
| ITGA2 | 6 | 12 | 1.03 | 3.60 | 5.01 | 5.29 | 4.71 | 14.20 |
| | | | — | 3.48 | 4.85 | 5.13 | 4.56 | 13.75 |

Example 2

Staining of Cancer Cells and Leukocytes Using Anti-TM4SF1 Antibody

In Example 1, the TM4SF1 gene was found to be more highly expressed in cancer cells than in leukocytes of healthy individuals. In view of this, whether TM4SF1 can be used for specific detection of tumor cells contained in a blood sample was studied.

(1) Erythrocytes were removed from blood of a healthy individual by a separation method based on the specific-gravity difference, to provide a blood sample to be used in the present Example. This sample was spiked with human lung adenocarcinoma cells (PC14) or human pancreatic cancer cells (PANC1).

(2) To 100 μL of the blood sample spiked with the cancer cell line, 10 μL of FcR Blocking Reagent (Miltenyi Biotec) was added, and blocking treatment was carried out at room temperature for 10 minutes.

(3) Thereafter, 10 μL of a solution of an antibody against TM4SF1 (Human TM4SF1 Phycoerythrin MAb, R&D systems), and 10 μL of a solution of an antibody against CD45 (CD45-FITC, Beckman Coulter) for detection of leukocytes were added, followed by incubation at room temperature for 30 minutes.

(4) Thereafter, the cells were washed three times with HBSS (Hank's Balanced Salt Solution) supplemented with 1% BSA and 5 mM EDTA, and then mounted on a slide glass using Permount Fisher (Fisher Scientific), followed by observation under a fluorescence microscope.

The results of staining of the human lung adenocarcinoma cells (PC14) are shown in FIG. 3, and the results of staining of the human pancreatic cancer cells (PANC1) are shown in FIG. 4. In the figures, the cells indicated by arrows are spiked cancer cells. According to the results in both FIG. 3 and FIG. 4, the cells stained with the antibody against TM4SF1 (anti-TM4SF1 antibody) (the cells indicated by arrows in FIG. 3(*a*) and FIG. 4(*a*)) were not stained with the antibody against CD45 (FIG. 3(*b*) and FIG. 4(*b*)). Thus, it can be seen that TM4SF1 (SEQ ID NO:1) can be used as a tumor marker for detection of tumor cells contained in a blood sample in distinction from leukocytes contained in the sample.

Example 3

Staining of Cancer Cells and Leukocytes Using Anti-TNFRSF12A Antibody

In Example 1, the TNFRSF12A gene was found to be more highly expressed in cancer cells than in leukocytes of healthy individuals. In view of this, whether TNFRSF12A can be used for specific detection of tumor cells contained in a blood sample was studied.

(1) Erythrocytes were removed from blood of a healthy individual by a separation method based on the specific-gravity difference, to provide a blood sample to be used in the present Example. This sample was spiked with human lung adenocarcinoma cells (PC9) or human breast adenocarcinoma cells (MDAMB231).

(2) To 100 μL of the blood sample spiked with the cancer cell line, 10 μL of FcR Blocking Reagent (Miltenyi Biotec) was added, and blocking treatment was carried out at room temperature for 10 minutes.

(3) Thereafter, 2.5 μL of a solution of an antibody against TNFRSF12A (PE anti-human CD266 (Fn14, TWEAK R) Antibody, Biolegend), and 10 μL of a solution of an antibody against CD45 (CD45-FITC, Beckman Coulter) for detection of leukocytes were added, followed by incubation at room temperature for 30 minutes.

(4) Thereafter, the cells were washed three times with HBSS (Hank's Balanced Salt Solution) supplemented with 1% BSA and 5 mM EDTA, and then mounted on a slide glass using Permount Fisher (Fisher Scientific), followed by observation under a fluorescence microscope.

The results of staining of the human lung adenocarcinoma cells (PC9) are shown in FIG. 5, and the results of staining of the human breast adenocarcinoma cells (MDAMB231) are shown in FIG. 6. In the figures, the cells indicated by arrows are spiked cancer cells. According to the results in both FIG. 5 and FIG. 6, the cells stained with the antibody against TNFRSF12A (anti-TNFRSF12A antibody) (the cells indicated by arrows in FIG. 5(*a*) and FIG. 6(*a*)) were not stained with the antibody against CD45 (FIG. 5(*b*) and FIG. 6(*b*)). Thus, it can be seen that TNFRSF12A (SEQ ID NO:2) can be used as a tumor marker for detection of tumor cells contained in a blood sample in distinction from leukocytes contained in the sample.

Example 4

Staining of Cancer Cells and Leukocytes Using Anti-F3 Antibody

In Example 1, the F3 gene was found to be more highly expressed in cancer cells than in leukocytes of healthy individuals. In view of this, whether F3 can be used for specific detection of tumor cells contained in a blood sample was studied.

(1) Erythrocytes were removed from blood of a healthy individual by a separation method based on the specific-gravity difference, to provide a blood sample to be used in the present Example. This sample was spiked with human lung adenocarcinoma cells (PC9) or human breast adenocarcinoma cells (MDAMB231).

(2) To 100 μL of the blood sample spiked with the cancer cell line, 10 μL of FcR Blocking Reagent (Miltenyi Biotec) was added, and blocking treatment was carried out at room temperature for 10 minutes.

(3) Thereafter, 10 μL of a solution of an antibody against F3 (CD142-FITC, Miltenyi Biotec), and 7 μL of a solution of an antibody against CD45 (CD45-PE, Beckman Coulter) for detection of leukocytes were added, followed by incubation at room temperature for 30 minutes.

(4) Thereafter, the cells were washed three times with HBSS (Hank's Balanced Salt Solution) supplemented with 1% BSA and 5 mM EDTA, and then mounted on a slide glass using Permount Fisher (Fisher Scientific), followed by observation under a fluorescence microscope.

The results of staining of the human lung adenocarcinoma cells (PC9) are shown in FIG. 7, and the results of staining of the human breast adenocarcinoma cells (MDAMB231) are shown in FIG. 8. In the figures, the cells indicated by arrows are spiked cancer cells. According to the results in both FIG. 7 and FIG. 8, the cells stained with the antibody against F3 (anti-F3 antibody) (the cells indicated by arrows in FIG. 7(*a*) and FIG. 8(*a*)) were not stained with the antibody against CD45 (FIG. 7(*b*) and FIG. 8(*b*)). Thus, it can be seen that F3 (SEQ ID NO:4) can be used as a tumor marker for detection of tumor cells contained in a blood sample in distinction from leukocytes contained in the sample.

Example 5

Staining of Cancer Cells and Leukocytes Using Anti-EPHA2 Antibody

In Example 1, the EPHA2 gene was found to be more highly expressed in prostate cancer cells than in leukocytes of healthy individuals. In view of this, whether EPHA2 can be used for specific detection of prostate cancer cells contained in a blood sample was studied.

(1) Erythrocytes were removed from blood of a healthy individual by a separation method based on the specific-gravity difference, to provide a blood sample to be used in the present Example. This sample was spiked with human prostate cancer cells (PC3).

(2) To 100 μL of the blood sample spiked with the cancer cell line, 10 μL of FcR Blocking Reagent (Miltenyi Biotec) was added, and blocking treatment was carried out at room temperature for 10 minutes.

(3) Thereafter, 5 μL of a solution of an antibody against EPHA2 (PE anti-human EphA2, Biolegend), and 10 μL of a solution of an antibody against CD45 (CD45-FITC, Beckman Coulter) for detection of leukocytes were added, followed by incubation at room temperature for 30 minutes.

(4) Thereafter, the cells were washed three times with HBSS (Hank's Balanced Salt Solution) supplemented with 1% BSA and 5 mM EDTA, and then mounted on a slide glass using Permount Fisher (Fisher Scientific), followed by observation under a fluorescence microscope.

The results of staining of the human prostate cancer cells (PC3) are shown in FIG. 9. In the figures, the cells indicated by arrows are spiked prostate cancer cells. According to the results in FIG. 9, the cells stained with the antibody against EPHA2 (anti-EPHA2 antibody) (the cells indicated by arrows in FIG. 9(*a*)) were not stained with the antibody against CD45 (FIG. 9(*b*)). Thus, it can be seen that EPHA2 (SEQ ID NO:5) can be used as a tumor marker for detection of prostate cancer cells contained in a blood sample in distinction from leukocytes contained in the sample.

Example 6

Staining of Cancer Cells and Leukocytes Using Anti-ITGA2 Antibody

In Example 1, the ITGA2 gene was found to be more highly expressed in pancreatic cancer cells than in leukocytes of healthy individuals. In view of this, whether ITGA2 can be used for specific detection of pancreatic cancer cells contained in a blood sample was studied.

(1) Erythrocytes were removed from blood of a healthy individual by a separation method based on the specific-gravity difference, to provide a blood sample to be used in the present Example. This sample was spiked with human pancreatic cancer cells (PANC1 or AsPC-1).

(2) To 100 μL of the blood sample spiked with the cancer cell line, 10 μL of FcR Blocking Reagent (Miltenyi Biotec) was added, and blocking treatment was carried out at room temperature for 10 minutes.

(3) Thereafter, 5 μL of a solution of an antibody against ITGA2 (FITC-anti-human ITGA2 Antibody, Biolegend), and 20 μL of a solution of an antibody against CD45 (CD45-PE, Beckman Coulter) for detection of leukocytes were added, followed by incubation at room temperature for 40 minutes.

(4) Thereafter, the cells were washed twice with HBSS (Hank's Balanced Salt Solution) supplemented with 1% BSA, 5 mM EDTA, and 6 μg/mL Tirofiban, and then plated on a slide glass, followed by observation under a fluorescence microscope.

The results of staining of the human pancreatic cancer cells PANC1 are shown in FIG. 10, and the results of staining of the human pancreatic cancer cells AsPC-1 are shown in FIG. 11. In the figures, the cells indicated by arrows are spiked pancreatic cancer cells. According to the results in both FIG. 10 and FIG. 11, the cells stained with the antibody against ITGA2 (anti-ITGA2 antibody) (the cells indicated by arrows in FIG. 10(*a*) and FIG. 11(*a*)) were not stained with the antibody against CD45 (FIG. 10(*b*) and FIG. 11(*b*)). Thus, it can be seen that ITGA2 (SEQ ID NO:6) can be used as a tumor marker for detection of pancreatic cancer cells contained in a blood sample in distinction from leukocytes contained in the sample.

Example 7

Staining of Cancer Cells Using Anti-TM4SF1 Antibody, Anti-TNFRSF12A Antibody, and Anti-EpCAM Antibody In Example 1, the TM4SF1 gene and the TNFRSF12A gene were found to be more highly expressed in cancer cells than in leukocytes of healthy individuals. In view of this, antibodies that recognize TM4SF1, TNFRSF12A, or an existing tumor marker EpCAM were employed to study whether TM4SF1 protein and TNFRSF12A protein can be used for detection of cancer cells. In the present Example, the cancer cell lines (10 lines) used in Example 1 were used as cancer cells.

(1) After adding 10 μL of FcR Blocking Reagent (Miltenyi Biotec) to 100 μL of a cancer cell line suspension ($2.5\times10^3$ cells/100 μL (PC-9 or PC-14) or $1\times10^4$ cells/100 μL (MDAMB231, SKBR3, PC-3, 22Rv1, HepG2, HuH-7, PANC-1, or AsPC-1)), blocking treatment was carried out at room temperature for 10 minutes.

(2) Thereafter, 10 μL of an anti-TM4SF1 antibody (PE-anti-human TM4SF1 Antibody, R&D systems), 2.5 μL of an anti-TNFRSF12A antibody (PE-anti-human TNFRSF12A Antibody, Biolegend), or 3 μL of an anti-EpCAM antibody (Alexa Fluoro 488-anti-human EpCAM Antibody, Biolegend) was added, and the resulting mixture was incubated at room temperature for 60 minutes.

(3) Thereafter, the cells were washed twice with HBSS (Hank's Balanced Salt Solution) supplemented with 1% BSA, 5 mM EDTA, and 6 μg/mL Tirofiban, and then plated on a slide glass, followed by observation under a fluorescence microscope.

The results of the staining of the cancer cells using the anti-TM4SF1 antibody, anti-TNFRSF12A antibody, or anti-EpCAM antibody are shown in Table 9. In the table, each staining result is represented as the intensity of the fluorescence signal (rated on a 5-point scale from "+" to "+++++") derived from each fluorescently labeled antibody. The higher the intensity of the signal (the larger the number of "+" symbols), the higher the expression (signal intensity (expression level): "+" <"++" <"+++" <"++++" <"+++++"). The results indicate that TM4SF1 protein (SEQ ID NO:1) and TNFRSF12A protein (SEQ ID NO:2) are expressed, irrespective of the cancer type, in lung adenocarcinoma cells, breast adenocarcinoma cells, breast cancer cells, prostate cancer cells, liver cancer cells, and pancreatic cancer cells. It can thus be seen that a wide range of tumor cells contained in a sample can be detected therewith. The results also suggest that a wide range of tumor cells contained in a sample can be collected with TM4SF1 protein or TNFRSF12A protein irrespective of the cancer type (lung cancer, breast adenocarcinoma, breast cancer, prostate cancer, liver cancer, or pancreatic cancer). Since high expression (with four or more "+" symbols) of TM4SF1 and/or TNFRSF12A was found also in the cell lines (PC-14, MDAMB231, PC-3, and PANC1) that exhibited low expression (with a single "+" symbol) of the existing tumor marker EpCAM, it is suggested that tumor cells contained in a sample can be accurately detected and collected by combination of TM4SF1 and/or TNFRSF12A with EpCAM.

TABLE 9

| | | Protein | | |
|---|---|---|---|---|
| cancer type | cancer cell line name | TM4SF1 (SEQ ID NO: 1) | TNFRSF12A (SEQ ID NO: 2) | EpCAM |
| lung | PC-9 | + | ++++ | +++++ |
| adenocarcinoma | PC-14 | +++++ | + | + |
| breast adenocarcinoma | MDAMB231 | +++ | +++++ | + |
| breast cancer | SKBR3 | ++ | ++ | +++++ |
| prostate cancer | PC-3 | ++ | ++++ | + |
| | 22Rv1 | + | + | +++++ |
| liver cancer | HepG2 | +++++ | +++ | +++ |
| | HuH-7 | +++++ | +++ | +++ |
| pancreatic | PANC1 | +++++ | +++++ | + |
| cancer | AsPC-1 | +++++ | +++++ | +++++ |

Example 8

Collection of Cancer Cells Using Anti-TM4SF1 Antibody, Anti-TNFRSF12A Antibody, and Anti-EpCAM Antibody In Example 7, TM4SF1 protein (SEQ ID NO:1) and TNFRSF12A protein (SEQ ID NO:2) were found to be highly expressed also in the cell lines (PC-14, MDAMB231, PC-3, and PANC1) that exhibited low expression of the existing tumor marker EpCAM protein. In view of this, whether cancer cells contained in a sample can be collected using antibodies that recognize TM4SF1 protein, TNFRSF12A protein, and the existing tumor marker EpCAM protein, respectively, was studied. In the present Example, a human pancreatic cancer cell line PANC1, which exhibits low expression of EpCAM protein, was used as cancer cells. The "buffer" used in the following procedure is D-PBS(−) (Dulbecco's Phosphate-Buffered Saline, $Mg^{2+}$- and $Ca^{2+}$-free) supplemented with 0.5% BSA and 2 mM EDTA.

(1) One milliliter of blood of a healthy individual was spiked with 100 μL (100 cells) of human pancreatic cancer cells (PANC1).

(2) To the spiked sample of (1), 10 mL of 1×BD Pharm Lyse (BD) was added, and the resulting mixture was incubated at room temperature for 10 minutes, followed by washing and suspending the cells in the buffer (3) To 100 μL of the cell suspension, 50 μL of FcR Blocking Reagent (Miltenyi Biotec) was added, and blocking treatment was carried out at room temperature for 10 minutes.

(4) Thereafter, one of, or all three of, 50 μL of an anti-TM4SF1 antibody (PE-anti-human TM4SF1 Antibody, R&D systems), 2.5 μL of an anti-TNFRSF12A antibody (PE-anti-human TNFRSF12A Antibody, Biolegend), and 10 μL of an anti-EpCAM antibody (PE-anti-human EpCAM Antibody, Miltenyi Biotec) was/were added, and the resulting mixture was incubated under refrigeration for 10 minutes, followed by washing and suspending the cells in the buffer.

(5) To 80 μL of the cell suspension, 20 μL of Anti-PE Microbeads UltraPure (Miltenyi Biotec) was added, and the resulting mixture was incubated under refrigeration for 15 minutes, followed by washing and suspending the cells in the buffer.

(6) An MS column (Miltenyi Biotec) was mounted on a MACS Separator (Miltenyi Biotec), and washed with the buffer.

(7) To the column of (6), 500 μL of the cell suspension was added, and the column was washed three times with 500 μL of the buffer.

(8) The column after the washing was removed from the MACS Separator, and 1 mL of the buffer was added into the column, followed by pushing a plunger into the column, to collect the cells.

(9) The collected cells were plated on a slide glass, and the number of the cells was counted under the microscope.

The results of the collection of the cancer cells by using one of, or all of, the anti-TM4SF1 antibody, anti-TNFRSF12A antibody, and anti-EpCAM antibody are shown in Table 10. In this table, the ratio of the number of collected cells to the number of spiked cells is represented as the cell collection ratio [%]. As a result, in the cases where the anti-TM4SF1 antibody or anti-TNFRSF12A antibody was used alone, higher cell collection ratios were found compared to the case where the anti-EpCAM antibody was used alone. Further, in the case where the three antibodies, that is, the anti-TM4SF1 antibody, anti-TNFRSF12A antibody, and anti-EpCAM antibody, were used together, an even higher cell collection ratio was found compared to the cases where they were used individually. From these results, it can be seen that TM4SF1 protein and TNFRSF12A protein enable highly efficient collection of cancer cells from a blood sample even when collection of the cancer cells with the existing marker EpCAM protein results in a low collection ratio. Further, it can be seen that combination of TM4SF1 protein and TNFRSF12A protein with EpCAM protein enables even more efficient collection of cancer cells even when collection of the cancer cells with EpCAM protein results in a low collection ratio.

TABLE 10

| antibody used | | | PANC1 cell |
|---|---|---|---|
| anti-EpCAM antibody | anti-TM4SF1 antibody | anti-TNFRSF12A antibody | collection ratio [%] |
| ○ | — | — | 49.0 |
| — | ○ | — | 66.0 |
| — | — | ○ | 74.1 |
| ○ | ○ | ○ | 82.1 |

Example 9

Staining of Cancer Cells Using Anti-SDC1 Antibody

In Example 1, the SDC1 gene was found to be more highly expressed in cancer cells than in leukocytes of healthy individuals. In view of this, an antibody that recognizes SDC1 was employed to study whether SDC1 can be used for detection of cancer cells. In the present Example, the cancer cell lines (10 lines) used in Example 1 were used as cancer cells.

(1) To 100 μL of a suspension of each cancer cell line ($1\times10^4$ cells/100 μL), 10 μL of FcR Blocking Reagent (Miltenyi Biotec) was added, and blocking treatment was carried out at room temperature for 10 minutes.

2) Thereafter, 10 μL of an anti-SDC1 antibody (PE-anti-human SDC1 Antibody, Miltenyi Biotec) was added, and the resulting mixture was incubated at room temperature for 60 minutes.

(3) Thereafter, the cells were washed twice with HBSS (Hank's Balanced Salt Solution) supplemented with 1% BSA, 5 mM EDTA, and 6μg/mL Tirofiban, and then plated on a slide glass, followed by observation under a fluorescence microscope.

The results of the staining of the cancer cells using the anti-SDC1 antibody are shown in Table 11. In the table, each staining result is represented as the intensity of the fluorescence signal (rated on a 5-point scale from "+" to "+++++") derived from each fluorescently labeled antibody. The higher the intensity of the signal (the larger the number of "+" symbols), the higher the expression (signal intensity (expression level): "+" <"++" <"+++" <"++++" <"+++++"). The results indicate that SDC1 protein (SEQ ID NO:3) is expressed, irrespective of the cancer type, in lung adenocarcinoma cells, breast adenocarcinoma cells, breast cancer cells, prostate cancer cells, liver cancer cells, and pancreatic cancer cells. It can thus be seen that a wide range of tumor cells contained in a sample can be detected therewith. The results also suggest that a wide range of tumor cells contained in a sample can be collected with SDC1 protein irrespective of the cancer type (lung cancer, breast adenocarcinoma, breast cancer, prostate cancer, liver cancer, or pancreatic cancer). Since high expression (with four or more "+" symbols) of SDC1 was found also in the cell lines (PC-14, MDAMB231, and PC-3) that exhibited low expression (with a single "+" symbol; see Table 9) of the existing tumor marker EpCAM, it is suggested that tumor cells contained in a sample can be accurately detected and collected by combination of SDC1 with EpCAM.

TABLE 11

| cancer type | cancer cell line name | Protein SDC1 (SEQ ID NO: 3) |
|---|---|---|
| lung adenocarcinoma | PC-9 | +++++ |
| | PC-14 | +++++ |
| breast adenocarcinoma | MDAMB231 | +++++ |
| breast cancer | SKBR3 | ++++ |
| prostate cancer | PC-3 | ++++ |
| | 22Rv1 | +++ |
| liver cancer | HepG2 | + |
| | HuH-7 | ++ |
| pancreatic cancer | PANC1 | ++ |
| | AsPC-1 | +++++ |

Example 10

Staining of Cancer Cells and Leukocytes Using Anti-SDC1 Antibody

In Example 1, the SDC1 gene was found to be more highly expressed in breast cancer or breast adenocarcinoma cells and pancreatic cancer cells than in leukocytes of healthy individuals. In view of this, whether SDC1 can be used for specific detection of breast cancer cells and pancreatic cancer cells contained in a blood sample was studied.

(1) Erythrocytes were removed from blood of a healthy individual by a separation method based on the specific-gravity difference, to provide a blood sample to be used in the present Example. This sample was spiked with human breast cancer cells (SKBR3) or human pancreatic cancer cells (AsPC-1).

(2) To 100 μL of the blood sample spiked with the cancer cell line, 10 μL of FcR Blocking Reagent (Miltenyi Biotec) was added, and blocking treatment was carried out at room temperature for 10 minutes.

(3) Thereafter, 10 μL of a solution of an antibody against SDC1 (PE-anti-human SDC1 Antibody, Miltenyi Biotec), and 10 μL of a solution of an antibody against CD45 (CD45-FITC, Biolegend) for detection of leukocytes were added, followed by incubation at room temperature for 40 minutes.

(4) Thereafter, the cells were washed twice with HBSS (Hank's Balanced Salt Solution) supplemented with 1% BSA, 5 mM EDTA, and 6 μg/mL Tirofiban, and then plated on a slide glass, followed by observation under a fluorescence microscope.

The results of staining of the human breast cancer cells SKBR3 are shown in FIG. 12, and the results of staining of the human pancreatic cancer cells AsPC-1 are shown in FIG. 13. In the figures, the cells indicated by arrows are spiked breast cancer cells and pancreatic cancer cells. According to the results in both FIG. 12 and FIG. 13, the cells stained with the antibody against SDC1 (anti-SDC1 antibody) (the cells indicated by arrows in FIG. 12(*a*) and FIG. 13(*a*)) were not stained with the antibody against CD45 (FIG. 12(*b*) and FIG. 13(*b*)). Thus, it can be seen that SDC1 (SEQ ID NO:3) can be used as a tumor marker for detection of breast cancer cells and pancreatic cancer cells contained in a blood sample in distinction from leukocytes contained in the sample.

Example 11

Collection of Cancer Cells Using Anti-TM4SF1 Antibody, Anti-TNFRSF 12A Antibody, Anti-SDC1 Antibody, and Anti-EpCAM Antibody In Example 7, TM4SF1 protein (SEQ ID NO:1) and TNFRSF12A protein (SEQ ID NO:2) were found, and, in Example 9, SDC1 protein (SEQ ID NO:3) was found, to be highly expressed also in the cell lines (PC-14, MDAMB231, and PC-3) that exhibited low expression of the existing tumor marker EpCAM protein. In view of this, whether cancer cells contained in a sample can be collected using antibodies that recognize TM4SF1 protein, TNFRSF12A protein, SDC1 protein, and the existing tumor marker EpCAM protein, respectively, was studied. In the present Example, a human prostate cancer cell line PC-3, which exhibits low expression of EpCAM protein, was used as cancer cells. The "buffer" used in the following procedure is D-PBS(−) (Dulbecco's Phosphate-Buffered Saline, $Mg^{2+}$- and $Ca^{2+}$-free) supplemented with 0.5% BSA and 2 mM EDTA.

(1) One milliliter of blood of a healthy individual was spiked with 100 μL (100 cells) of a human prostate cancer cell line (PC-3).

(2) To the spiked sample of (1), 10 mL of 1×BD Pharm Lyse (BD) was added, and the resulting mixture was incubated at room temperature for 10 minutes, followed by washing and suspending the cells in the buffer (3) To 100 μL of the cell suspension, 50 μL of FcR Blocking Reagent (Miltenyi Biotec) was added, and blocking treatment was carried out at room temperature for 10 minutes.

(4) Thereafter, one of, the three other than the anti-EpCAM antibody of, or all four of, 50 μL of an anti-TM4SF1 antibody (PE-anti-human TM4SF1 Antibody, R&D systems), 2.5 μL of an anti-TNFRSF12A antibody (PE-anti-human TNFRSF12A Antibody, Biolegend), 5 μL of an anti-SDC1 antibody (PE-anti-human SDC1 Antibody, Biolegend), and 10 μL of an anti-EpCAM antibody (PE-anti-human EpCAM Antibody, Miltenyi Biotec) was/were added, and the resulting mixture was incubated under refrigeration for 10 minutes, followed by washing and suspending the cells in the buffer.

(5) To 80 μL of the cell suspension, 20 μL of Anti-PE Microbeads UltraPure (Miltenyi Biotec) was added, and the resulting mixture was incubated under refrigeration for 15 minutes, followed by washing and suspending the cells in the buffer.

(6) An MS column (Miltenyi Biotec) was mounted on a MACS Separator (Miltenyi Biotec), and washed with the buffer.

(7) To the column of (6), 500 μL of the cell suspension was added, and the column was washed three times with 500 μL of the buffer.

(8) The column after the washing was removed from the MACS Separator, and 1 mL of the buffer was added into the column, followed by pushing a plunger into the column, to collect the cells.

(9) The collected cells were plated on a slide glass, and the number of the cells was counted under the microscope.

The results of the collection of the cancer cells by using one of, the three other than the anti-EpCAM antibody of, or all four of, the anti-TM4SF1 antibody, anti-TNFRSF12A antibody, anti-SDC1 antibody, and anti-EpCAM antibody are shown in Table 12. In this table, the ratio of the number of collected cells to the number of spiked cells is represented as the cell collection ratio [%]. As a result, in the cases where the anti-TM4SF1 antibody, anti-TNFRSF12A antibody, or anti-SDC1 antibody was used alone, higher cell collection ratios were found compared to the case where the anti-EpCAM antibody was used alone. Further, in the cases where the three other than the anti-EpCAM antibody, or all four antibodies, were used, even higher cell collection ratios were found compared to the cases where they were used individually. Further, in the case where all four antibodies were used, a higher cell collection ratio was found compared to the case where the three other than the anti-EpCAM antibody was used. From these results, it can be seen that TM4SF1 protein, TNFRSF12A protein, and SDC1 protein enable highly efficient collection of cancer cells from a blood sample even when collection of the cancer cells with the existing marker EpCAM protein results in a low collection ratio. Further, it can be seen that combination of TM4SF1 protein, TNFRSF12A protein, and SDC1 protein with EpCAM protein enables even more efficient collection of cancer cells even when collection of the cancer cells with EpCAM protein results in a low collection ratio.

TABLE 12

| antibody used | | | | PC3 cell |
| --- | --- | --- | --- | --- |
| anti-EpCAM antibody | anti-TM4SF1 antibody | anti-TNFRSF12A antibody | anti-SDC1 antibody | collection ratio [%] |
| ○ | — | — | — | 42.0 |
| — | ○ | — | — | 76.0 |
| — | — | ○ | — | 48.0 |
| — | — | — | ○ | 64.0 |
| — | ○ | ○ | ○ | 83.0 |
| ○ | ○ | ○ | ○ | 91.0 |

The present invention is described above in detail with reference to particular embodiments. However, it is evident to those skilled in the art that the embodiments may be changed or modified in various ways without departing from the spirit and scope of the present invention.

The descriptions, sequence listings, claims, drawings, and abstracts of Japanese Patent Application No. 2018-042710 filed on Mar. 9, 2018, Japanese Patent Application No. 2018-105966 filed on Jun. 1, 2018, and Japanese Patent Application No. 2018-193273 filed on Oct. 12, 2018 are herein cited in their entirety to incorporate them in disclosure of the description of the present invention.

The invention claimed is:

1. A method of detecting a tumor cell contained in a sample in distinction from a contaminant cell, the method comprising detecting one or more polypeptides selected from the group consisting of the following (i) to (iii) present in the sample:

(i) a polypeptide comprising at least the amino acid sequence of any of SEQ ID NOs: 1 to 3;

(ii) a polypeptide comprising an amino acid sequence having a homology of not less than 85% to the amino acid sequence of any of SEQ ID NOs: 1 to 3; and (iii) a polypeptide comprising at least a splicing variant of the amino acid sequence of any of SEQ ID NOs: 1 to 3, or a polypeptide comprising at least a splicing variant of a polypeptide having a homology of not less than 85% to the amino acid sequence of any of SEQ ID NOs: 1 to 3, and wherein the tumor cell is an EpCAM (Epithelial Cell Adhesion Molecule)-negative tumor cell.

2. The method according to claim 1, wherein the detection is carried out using an antibody or aptamer that specifically recognizes one or more polypeptides selected from the group consisting of (i) to (iii).

3. A method of detecting a tumor cell contained in a sample in distinction from a contaminant cell, the method comprising detecting a gene encoding any of the following polypeptides (i) to (iii) present in the sample:

(i) a polypeptide comprising at least the amino acid sequence of any of SEQ ID NOs: 1 to 3;

(ii) a polypeptide comprising an amino acid sequence having a homology of not less than 85% to the amino acid sequence of any of SEQ ID NOs: 1 to 3; and (iii) a polypeptide comprising at least a splicing variant of the amino acid sequence of any of SEQ ID NOs: 1 to 3, or a polypeptide comprising at least a splicing variant of a polypeptide having a homology of not less than 85% to the amino acid sequence of any of SEQ ID NOs: 1 to 3, and wherein the tumor cell is an EpCAM (Epithelial Cell Adhesion Molecule)-negative tumor cell.

4. A method of collecting a tumor cell, the method comprising:

detecting a tumor cell contained in a sample in distinction from contaminant cell; and collecting the detected tumor cell using collection means;

wherein the detection of the tumor cell is carried out by detecting one or more polypeptides selected from the group consisting of the following (i) to (iii) present in the sample:

(i) a polypeptide comprising at least the amino acid sequence of any of SEQ ID NOs: 1 to 3;

(ii) a polypeptide comprising at least an amino acid sequence having a homology of not less than 85% to the amino acid sequence of any of SEQ ID NOs: 1 to 3; and (iii) a polypeptide comprising at least a splicing variant of the amino acid sequence of any of SEQ ID NOs: 1 to 3, or a polypeptide comprising at least a splicing variant of a polypeptide having a homology of not less than 85% to the amino acid sequence of any of SEQ ID NOs: 1 to 3, and wherein the tumor cell is an EpCAM (Epithelial Cell Adhesion Molecule)-negative tumor cell.

5. The method according to claim 4, wherein the detection of the tumor cell is carried out using an antibody or aptamer that specifically recognizes one or more polypeptides selected from the group consisting of (i) to (iii).

6. The method according to claim 1, wherein the sample is blood, and the contaminant cell contained in the sample is leukocyte.

* * * * *